(12) United States Patent
Heineman

(10) Patent No.: US 7,612,769 B2
(45) Date of Patent: Nov. 3, 2009

(54) COMPUTER-IMPLEMENTED METHODS FOR ORGANIZING IMAGE DATA PRODUCED BY RESONANT MIE SCATTERING OF LIGHT FROM MICROPARTICLES AND RESULTING DATA STRUCTURES

(75) Inventor: Lee J Heineman, Philadelphia, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 901 days.

(21) Appl. No.: 11/224,600

(22) Filed: Sep. 12, 2005

(65) Prior Publication Data
US 2006/0066851 A1 Mar. 30, 2006

Related U.S. Application Data

(60) Provisional application No. 60/609,758, filed on Sep. 14, 2004.

(51) Int. Cl.
*G06F 3/038* (2006.01)

(52) U.S. Cl. .......... 345/204; 345/208

(58) Field of Classification Search ......... 345/103–107, 345/204–215; 436/518–546
See application file for complete search history.

(56) References Cited

U.S. PATENT DOCUMENTS

| | | | |
|---|---|---|---|
| 6,169,816 B1 | 1/2001 | Ravkin | |
| 6,180,415 B1 * | 1/2001 | Schultz et al. | 436/518 |
| 6,200,820 B1 * | 3/2001 | Hansen et al. | 436/523 |
| 6,214,560 B1 * | 4/2001 | Yguerabide et al. | 506/3 |
| 6,259,807 B1 | 7/2001 | Ravkin | |
| 6,654,505 B2 | 11/2003 | Bridgham et al. | |
| 2002/0081014 A1 | 6/2002 | Ravkin | |
| 2003/0068638 A1 | 4/2003 | Cork et al. | |

FOREIGN PATENT DOCUMENTS

WO    WO 2004/044232    5/2004

* cited by examiner

*Primary Examiner*—Vijay Shankar

(57) ABSTRACT

A digital representation of an image produced on an electronic image plane by light scattered from one or more substantially spherical microparticles at each of a predetermined number (Q) of illuminating wavelengths is created. For each of the N pixels in each image an associated Image Intensity Data Array containing Q values is created. In one embodiment the resulting data structure is an inclusive collection of Pixel Records from each pixel in the image. In a second embodiment a select set of S number of Image Intensity Data Arrays is chosen. Each Image Intensity Data Array in the select set has at least one intensity value that exceeds a predetermined analog threshold. A Pointer Array containing N values is also created. The Pointer Array correlates the position on the electronic image plane of the pixel associated with each Image Intensity Data Array in the select set with the order of selection of that data array into the select set.

14 Claims, 28 Drawing Sheets

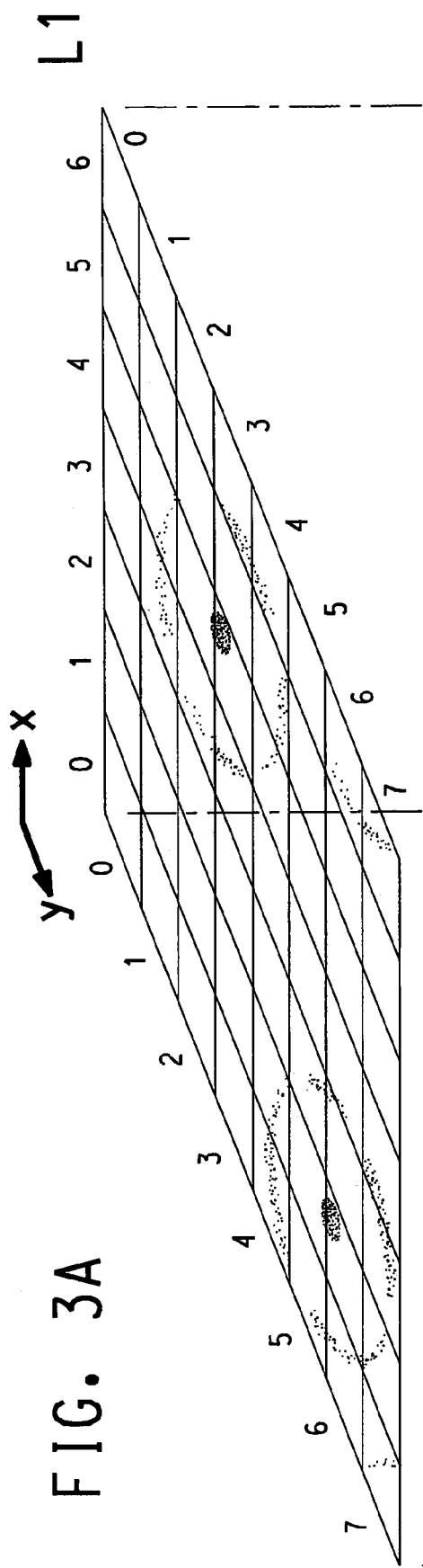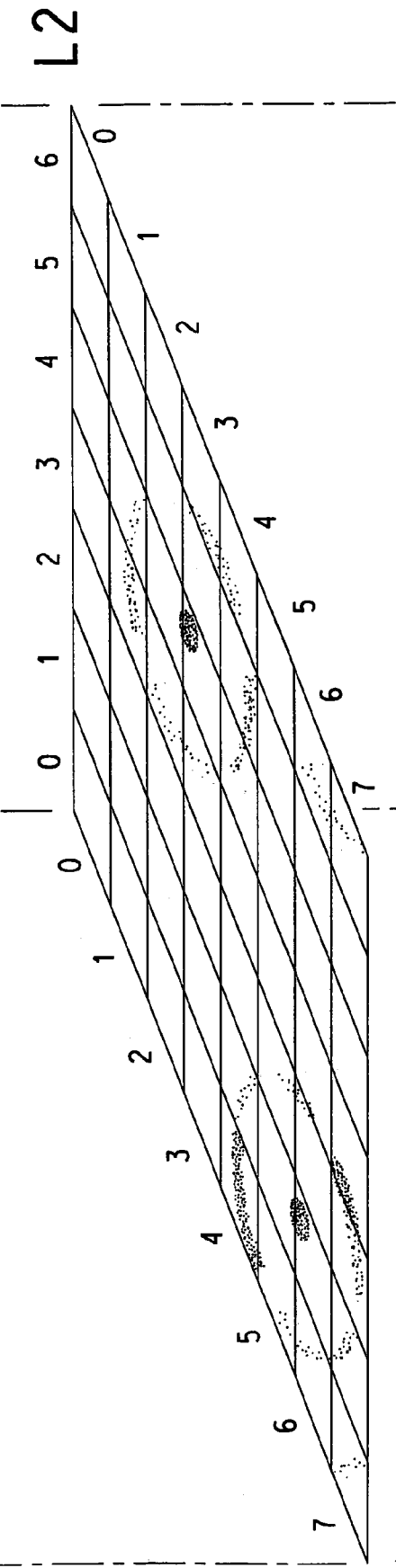
FIG. 3A
Continued on Fig. 3B

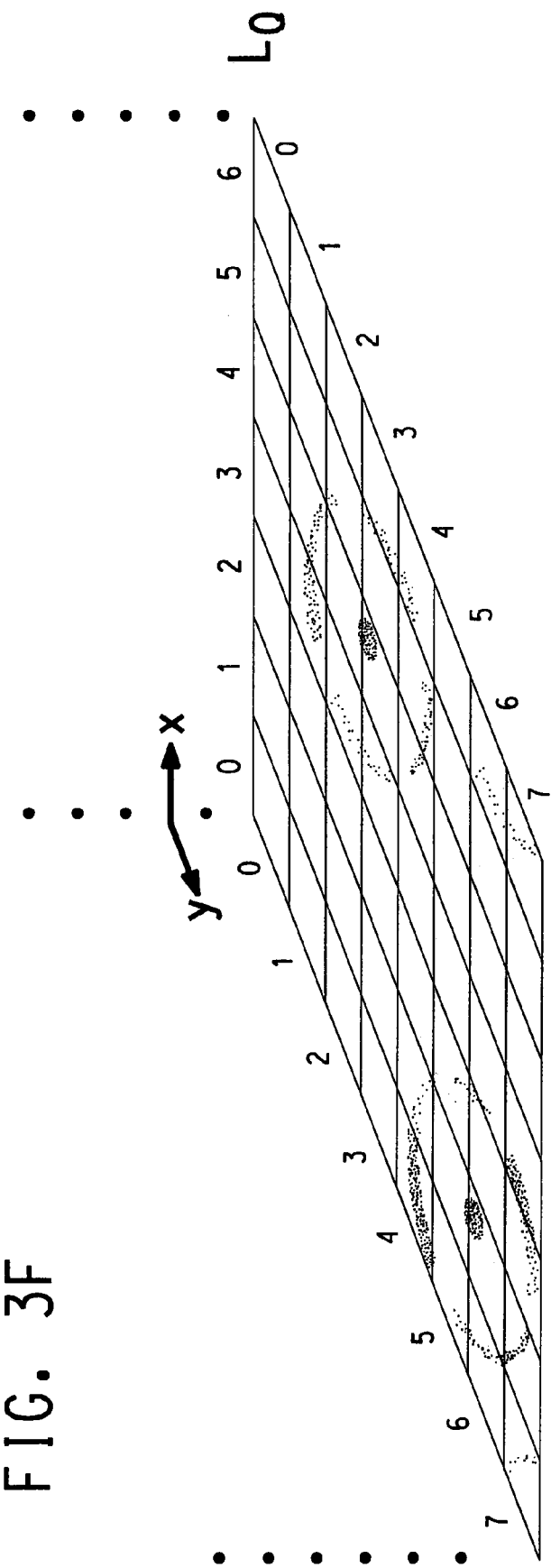
FIG. 3F
Continued from Fig. 3E

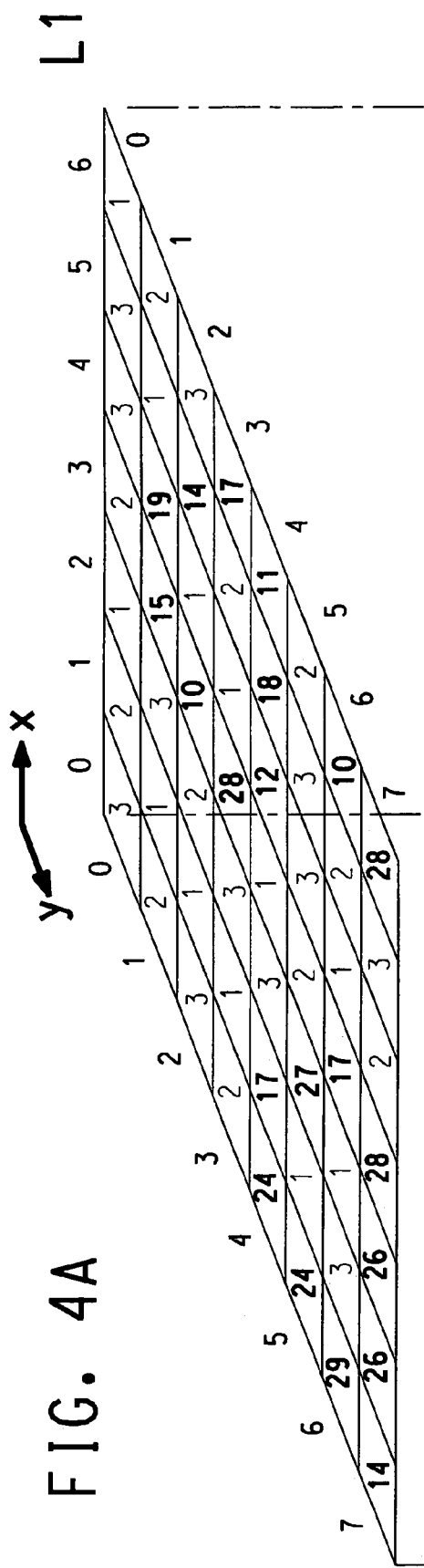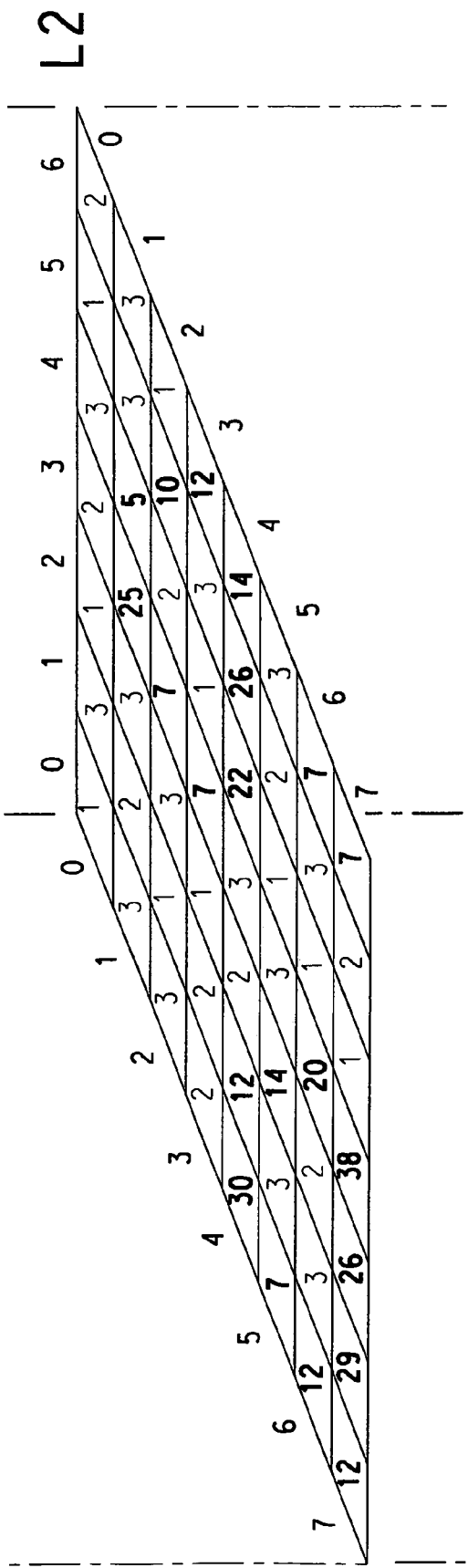
FIG. 4A

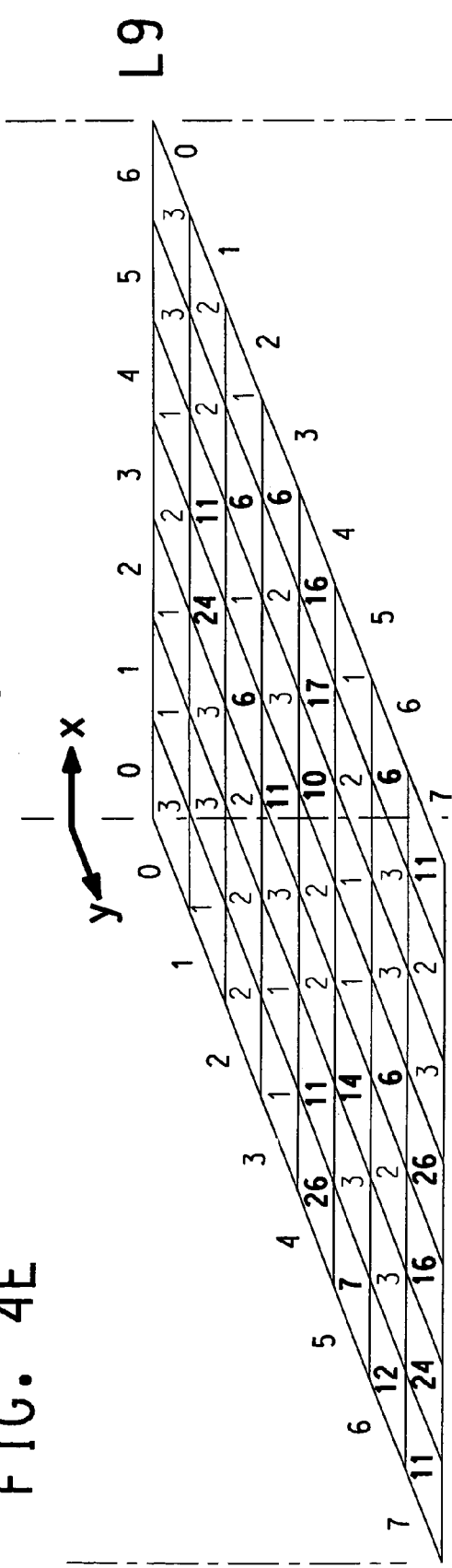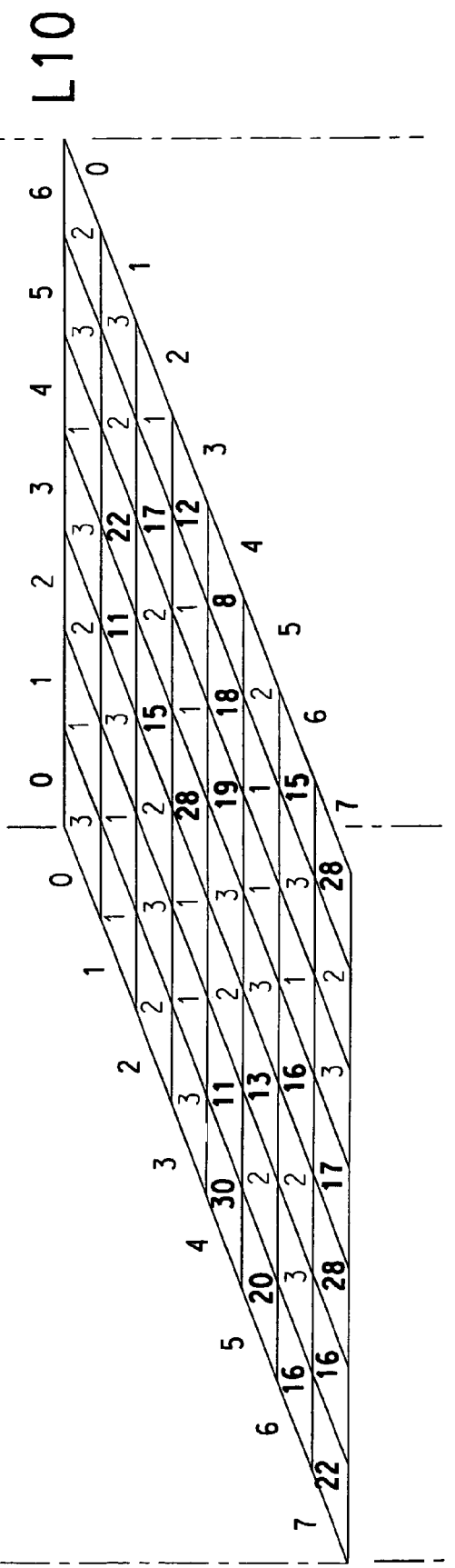
FIG. 4E

FIG. 7A
Table I
Image Intensity Data Arrays

| Location | 0,0 | 1,0 | 2,0 | 3,0 | 4,0 | 5,0 | 6,0 |
|---|---|---|---|---|---|---|---|
| L₁ | 3 | 2 | 1 | 2 | 3 | 3 | 1 |
| L₂ | 1 | 3 | 1 | 2 | 3 | 1 | 2 |
| L₃ | 2 | 1 | 2 | 1 | 3 | 1 | 1 |
| L₄ | 3 | 2 | 1 | 3 | 2 | 1 | 3 |
| L₅ | 1 | 3 | 2 | 2 | 3 | 1 | 3 |
| L₆ | 3 | 2 | 3 | 1 | 2 | 1 | 3 |
| L₇ | 1 | 1 | 2 | 2 | 2 | 1 | 3 |
| L₈ | 2 | 1 | 3 | 1 | 2 | 3 | 2 |
| L₉ | 3 | 1 | 2 | 3 | 1 | 3 | 3 |
| L₁₀ | 3 | 1 | 2 | 2 | 3 | 3 | 2 |
| L_q | 1 | 3 | 1 | 2 | 3 | 2 | 3 |

| Location | 0,1 | 1,1 | 2,1 | 3,1 | 4,1 | 5,1 | 6,1 |
|---|---|---|---|---|---|---|---|
| L₁ | 2 | 1 | 3 | 15 | 19 | 1 | 2 |
| L₂ | 3 | 2 | 3 | 25 | 5 | 3 | 3 |
| L₃ | 1 | 1 | 1 | 18 | 8 | 1 | 2 |
| L₄ | 3 | 1 | 2 | 18 | 26 | 2 | 3 |
| L₅ | 2 | 2 | 2 | 18 | 14 | 1 | 2 |
| L₆ | 3 | 3 | 1 | 23 | 28 | 3 | 3 |
| L₇ | 1 | 3 | 1 | 11 | 24 | 3 | 2 |
| L₈ | 1 | 1 | 3 | 25 | 14 | 2 | 1 |
| L₉ | 3 | 2 | 3 | 24 | 11 | 2 | 2 |
| L₁₀ | 1 | 1 | 2 | 11 | 22 | 2 | 3 |
| L_q | 3 | 2 | 2 | 24 | 20 | 1 | 2 |

| Location | 0,2 | 1,2 | 2,2 | 3,2 | 4,2 | 5,2 | 6,2 |
|---|---|---|---|---|---|---|---|
| L₁ | 3 | 1 | 2 | 10 | 1 | 14 | 3 |
| L₂ | 3 | 1 | 3 | 7 | 2 | 10 | 1 |
| L₃ | 2 | 1 | 2 | 11 | 1 | 3 | 3 |
| L₄ | 3 | 2 | 3 | 6 | 2 | 21 | 1 |
| L₅ | 1 | 2 | 1 | 6 | 3 | 9 | 3 |
| L₆ | 1 | 3 | 2 | 8 | 3 | 23 | 1 |
| L₇ | 1 | 2 | 1 | 12 | 3 | 19 | 1 |
| L₈ | 1 | 2 | 3 | 11 | 1 | 9 | 3 |
| L₉ | 2 | 2 | 2 | 6 | 2 | 6 | 1 |
| L₁₀ | 2 | 3 | 2 | 15 | 3 | 17 | 1 |
| L_q | 3 | 1 | 1 | 13 | 3 | 15 | 3 |

| Location | 0,3 | 1,3 | 2,3 | 3,3 | 4,3 | 5,3 | 6,3 |
|---|---|---|---|---|---|---|---|
| L₁ | 2 | 1 | 3 | 28 | 1 | 2 | 17 |
| L₂ | 2 | 2 | 1 | 7 | 1 | 3 | 12 |
| L₃ | 2 | 3 | 2 | 12 | 3 | 2 | 1 |
| L₄ | 1 | 2 | 1 | 36 | 1 | 3 | 14 |
| L₅ | 1 | 3 | 2 | 5 | 2 | 1 | 13 |
| L₆ | 2 | 1 | 3 | 10 | 2 | 1 | 14 |
| L₇ | 3 | 2 | 3 | 28 | 3 | 3 | 14 |
| L₈ | 1 | 3 | 1 | 10 | 2 | 2 | 10 |
| L₉ | 1 | 1 | 2 | 11 | 3 | 2 | 6 |
| L₁₀ | 3 | 1 | 1 | 28 | 1 | 1 | 12 |
| L_q | 2 | 2 | 2 | 10 | 3 | 1 | 14 |

FIG. 7B

Table I (continued)
Image Intensity Data Arrays

| Location | 0,4 | 1,4 | 2,4 | 3,4 | 4,4 | 5,4 | 6,4 |
|---|---|---|---|---|---|---|---|
| $L_1$ | 24 | 17 | 3 | 1 | 12 | 18 | 11 |
| $L_2$ | 30 | 12 | 2 | 3 | 22 | 26 | 14 |
| $L_3$ | 24 | 6 | 1 | 3 | 10 | 14 | 13 |
| $L_4$ | 24 | 26 | 2 | 2 | 13 | 10 | 15 |
| $L_5$ | 26 | 15 | 1 | 2 | 28 | 22 | 17 |
| $L_6$ | 22 | 14 | 2 | 1 | 10 | 18 | 13 |
| $L_7$ | 23 | 23 | 1 | 2 | 17 | 12 | 9 |
| $L_8$ | 34 | 14 | 2 | 2 | 32 | 25 | 14 |
| $L_9$ | 26 | 11 | 2 | 3 | 10 | 17 | 16 |
| $L_{10}$ | 30 | 11 | 3 | 1 | 19 | 18 | 8 |
| $L_q$ | 36 | 12 | 3 | 1 | 32 | 24 | 19 |

| Location | 0,5 | 1,5 | 2,5 | 3,5 | 4,5 | 5,5 | 6,5 |
|---|---|---|---|---|---|---|---|
| $L_1$ | 24 | 1 | 27 | 2 | 3 | 3 | 2 |
| $L_2$ | 7 | 3 | 14 | 3 | 1 | 2 | 3 |
| $L_3$ | 16 | 3 | 6 | 2 | 1 | 3 | 2 |
| $L_4$ | 25 | 2 | 14 | 3 | 1 | 2 | 3 |
| $L_5$ | 8 | 3 | 10 | 2 | 1 | 3 | 1 |
| $L_6$ | 7 | 2 | 2 | 3 | 3 | 2 | 3 |
| $L_7$ | 32 | 3 | 14 | 2 | 2 | 3 | 1 |
| $L_8$ | 11 | 2 | 13 | 2 | 1 | 2 | 3 |
| $L_9$ | 7 | 3 | 14 | 1 | 1 | 2 | 1 |
| $L_{10}$ | 20 | 2 | 13 | 3 | 1 | 3 | 2 |
| $L_q$ | 12 | 2 | 12 | 2 | 2 | 3 | 1 |

| Location | 0,6 | 1,6 | 2,6 | 3,6 | 4,6 | 5,6 | 6,6 |
|---|---|---|---|---|---|---|---|
| $L_1$ | 29 | 3 | 1 | 17 | 1 | 2 | 10 |
| $L_2$ | 12 | 3 | 2 | 20 | 1 | 3 | 7 |
| $L_3$ | 5 | 1 | 3 | 14 | 1 | 1 | 11 |
| $L_4$ | 30 | 3 | 3 | 16 | 2 | 1 | 6 |
| $L_5$ | 13 | 3 | 2 | 16 | 1 | 3 | 6 |
| $L_6$ | 12 | 1 | 1 | 14 | 2 | 1 | 8 |
| $L_7$ | 37 | 1 | 3 | 18 | 3 | 1 | 12 |
| $L_8$ | 16 | 1 | 3 | 19 | 2 | 3 | 11 |
| $L_9$ | 12 | 3 | 2 | 6 | 3 | 3 | 6 |
| $L_{10}$ | 25 | 3 | 2 | 16 | 1 | 3 | 15 |
| $L_q$ | 17 | 1 | 3 | 18 | 3 | 1 | 13 |

| Location | 0,7 | 1,7 | 2,7 | 3,7 | 4,7 | 5,7 | 6,7 |
|---|---|---|---|---|---|---|---|
| $L_1$ | 19 | 26 | 26 | 28 | 2 | 3 | 28 |
| $L_2$ | 5 | 29 | 26 | 38 | 1 | 2 | 7 |
| $L_3$ | 8 | 13 | 22 | 25 | 1 | 3 | 12 |
| $L_4$ | 26 | 22 | 19 | 30 | 2 | 3 | 36 |
| $L_5$ | 14 | 25 | 27 | 34 | 3 | 2 | 5 |
| $L_6$ | 28 | 13 | 17 | 16 | 2 | 1 | 10 |
| $L_7$ | 24 | 22 | 17 | 24 | 1 | 1 | 28 |
| $L_8$ | 14 | 35 | 35 | 34 | 3 | 2 | 10 |
| $L_9$ | 11 | 24 | 24 | 26 | 3 | 2 | 11 |
| $L_{10}$ | 22 | 16 | 16 | 17 | 3 | 2 | 28 |
| $L_q$ | 20 | 37 | 37 | 36 | 1 | 2 | 10 |

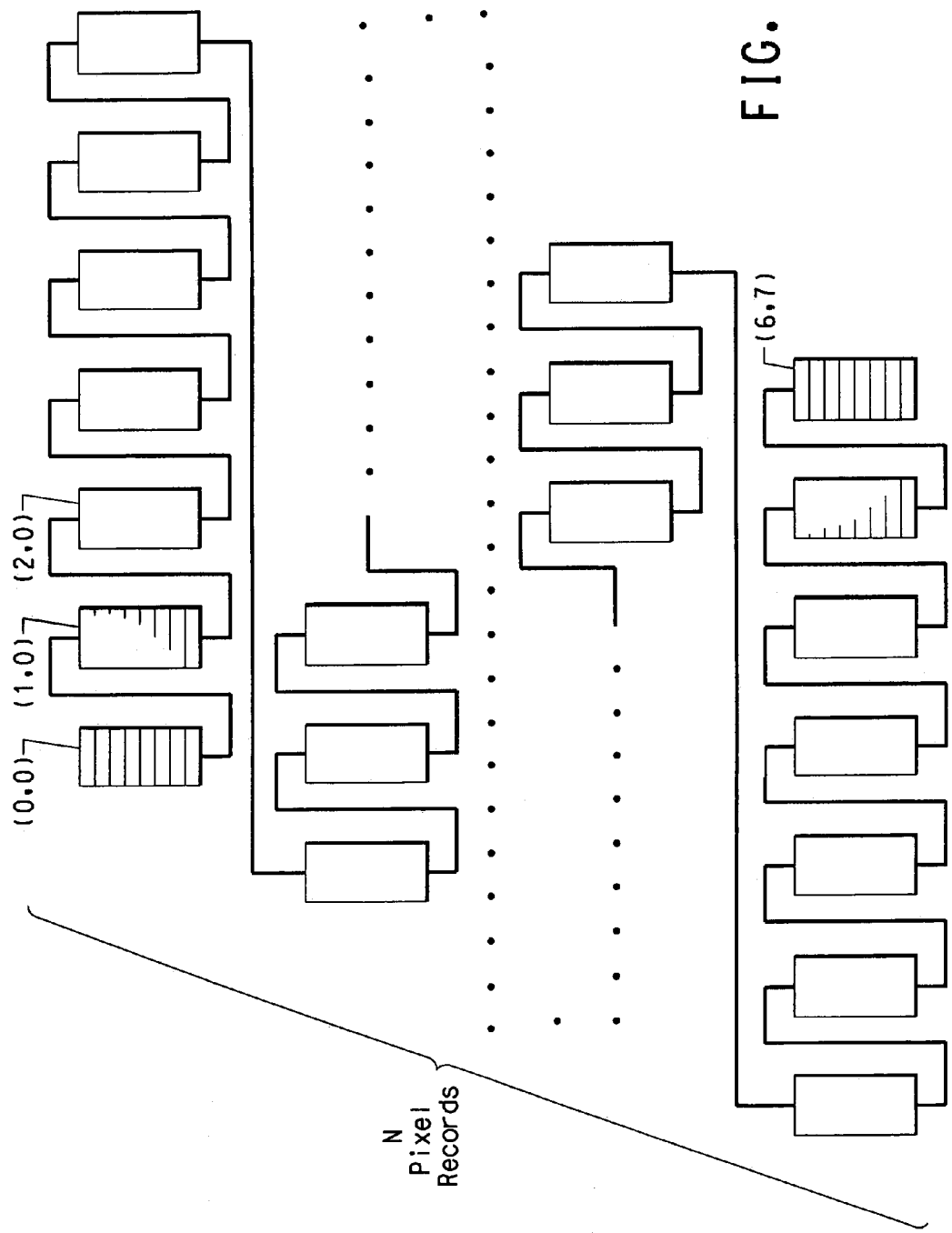

FIG. 9

Table II
Composite Maximum Image Array

| | | | | | | |
|---|---|---|---|---|---|---|
| 0,0<br>3 | 1,0<br>3 | 2,0<br>3 | 3,0<br>3 | 4,0<br>3 | 5,0<br>3 | 6,0<br>3 |
| 0,1<br>3 | 1,1<br>3 | 2,1<br>3 | 3,1<br>25 | 4,1<br>28 | 5,1<br>3 | 6,1<br>3 |
| 0,2<br>3 | 1,2<br>3 | 2,2<br>3 | 3,2<br>15 | 4,2<br>3 | 5,2<br>23 | 6,2<br>3 |
| 0,3<br>3 | 1,3<br>3 | 2,3<br>3 | 3,3<br>36 | 4,3<br>3 | 5,3<br>3 | 6,3<br>17 |
| 0,4<br>36 | 1,4<br>26 | 2,4<br>3 | 3,4<br>3 | 4,4<br>32 | 5,4<br>26 | 6,4<br>19 |
| 0,5<br>32 | 1,5<br>3 | 2,5<br>27 | 3,5<br>3 | 4,5<br>3 | 5,5<br>3 | 6,5<br>3 |
| 0,6<br>37 | 1,6<br>3 | 2,6<br>3 | 3,6<br>20 | 4,6<br>3 | 5,6<br>3 | 6,6<br>15 |
| 0,7<br>28 | 1,7<br>37 | 2,7<br>37 | 3,7<br>38 | 4,7<br>3 | 5,7<br>3 | 6,7<br>36 |

FIG. 10

Table III
Composite Minimum Image Array

| | | | | | | |
|---|---|---|---|---|---|---|
| 0,0<br>1 | 1,0<br>1 | 2,0<br>1 | 3,0<br>1 | 4,0<br>1 | 5,0<br>1 | 6,0<br>1 |
| 0,1<br>1 | 1,1<br>1 | 2,1<br>1 | 3,1<br>11 | 4,1<br>11 | 5,1<br>1 | 6,1<br>1 |
| 0,2<br>1 | 1,2<br>1 | 2,2<br>1 | 3,2<br>6 | 4,2<br>1 | 5,2<br>6 | 6,2<br>1 |
| 0,3<br>1 | 1,3<br>1 | 2,3<br>1 | 3,3<br>5 | 4,3<br>1 | 5,3<br>1 | 6,3<br>6 |
| 0,4<br>22 | 1,4<br>6 | 2,4<br>1 | 3,4<br>1 | 4,4<br>10 | 5,4<br>10 | 6,4<br>8 |
| 0,5<br>7 | 1,5<br>1 | 2,5<br>2 | 3,5<br>1 | 4,5<br>1 | 5,5<br>1 | 6,5<br>1 |
| 0,6<br>5 | 1,6<br>1 | 2,6<br>1 | 3,6<br>6 | 4,6<br>1 | 5,6<br>1 | 6,6<br>6 |
| 0,7<br>5 | 1,7<br>13 | 2,7<br>16 | 3,7<br>17 | 4,7<br>1 | 5,7<br>1 | 6,7<br>5 |

FIG. 11

Table IV
Composite Average Image Array

| | | | | | | |
|---|---|---|---|---|---|---|
| 0,0<br>2 | 1,0<br>2 | 2,0<br>2 | 3,0<br>2 | 4,0<br>3 | 5,0<br>2 | 6,0<br>2 |
| 0,1<br>2 | 1,1<br>2 | 2,1<br>2 | 3,1<br>19 | 4,1<br>17 | 5,1<br>2 | 6,1<br>2 |
| 0,2<br>2 | 1,2<br>2 | 2,2<br>2 | 3,2<br>10 | 4,2<br>2 | 5,2<br>13 | 6,2<br>2 |
| 0,3<br>2 | 1,3<br>2 | 2,3<br>2 | 3,3<br>17 | 4,3<br>2 | 5,3<br>2 | 6,3<br>12 |
| 0,4<br>27 | 1,4<br>15 | 2,4<br>2 | 3,4<br>2 | 4,4<br>19 | 5,4<br>19 | 6,4<br>14 |
| 0,5<br>15 | 1,5<br>3 | 2,5<br>13 | 3,5<br>2 | 4,5<br>2 | 5,5<br>3 | 6,5<br>2 |
| 0,6<br>19 | 1,6<br>2 | 2,6<br>2 | 3,6<br>16 | 4,6<br>2 | 5,6<br>2 | 6,6<br>10 |
| 0,7<br>16 | 1,7<br>23 | 2,7<br>23 | 3,7<br>28 | 4,7<br>2 | 5,7<br>2 | 6,7<br>17 |

FIG. 14

Table V
Analog Threshold Array
Threshold is 20

| Order of Selection Location | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
|  | 3,1 | 4,1 | 5,2 | 3,3 | 0,4 | 1,4 | 4,4 | 5,4 | 0,5 | 2,5 | 0,6 | 3,6 | 0,7 | 1,7 | 2,7 | 3,7 | 6,7 |
| $L_1$ | 15 | 19 | 14 | 28 | 24 | 17 | 12 | 18 | 24 | 27 | 29 | 17 | 19 | 26 | 26 | 28 | 28 |
| $L_2$ | 25 | 5 | 10 | 7 | 30 | 12 | 22 | 26 | 7 | 14 | 12 | 20 | 5 | 29 | 26 | 38 | 7 |
| $L_3$ | 18 | 8 | 3 | 12 | 24 | 6 | 10 | 14 | 16 | 6 | 5 | 14 | 8 | 13 | 22 | 25 | 12 |
| $L_4$ | 18 | 26 | 21 | 36 | 24 | 26 | 13 | 10 | 25 | 14 | 30 | 16 | 26 | 22 | 19 | 30 | 36 |
| $L_5$ | 18 | 14 | 9 | 5 | 26 | 15 | 28 | 22 | 8 | 10 | 13 | 16 | 14 | 25 | 27 | 34 | 5 |
| $L_6$ | 23 | 28 | 23 | 10 | 22 | 14 | 10 | 18 | 7 | 2 | 12 | 14 | 28 | 13 | 17 | 16 | 10 |
| $L_7$ | 11 | 24 | 19 | 28 | 23 | 23 | 17 | 12 | 32 | 14 | 37 | 18 | 24 | 22 | 17 | 24 | 28 |
| $L_8$ | 25 | 14 | 9 | 10 | 34 | 14 | 32 | 25 | 11 | 13 | 16 | 19 | 14 | 35 | 35 | 34 | 10 |
| $L_9$ | 24 | 11 | 6 | 11 | 26 | 11 | 10 | 17 | 7 | 14 | 12 | 6 | 11 | 24 | 24 | 26 | 11 |
| $L_{10}$ | 11 | 22 | 17 | 28 | 30 | 11 | 19 | 18 | 20 | 13 | 25 | 16 | 22 | 16 | 16 | 17 | 28 |
| $L_Q$ | 24 | 20 | 15 | 10 | 36 | 12 | 32 | 24 | 12 | 12 | 17 | 18 | 20 | 37 | 37 | 36 | 10 |

FIG. 16

Table VI
Composite Thresholded Image Array

| | | | | | | |
|---|---|---|---|---|---|---|
| 0,0 0 | 1,0 0 | 2,0 0 | 3,0 0 | 4,0 0 | 5,0 0 | 6,0 0 |
| 0,1 0 | 1,1 0 | 2,1 0 | 3,1 25 | 4,1 28 | 5,1 0 | 6,1 0 |
| 0,2 0 | 1,2 0 | 2,2 0 | 3,2 15 | 4,2 0 | 5,2 23 | 6,2 0 |
| 0,3 0 | 1,3 0 | 2,3 0 | 3,3 36 | 4,3 0 | 5,3 0 | 6,3 17 |
| 0,4 36 | 1,4 26 | 2,4 0 | 3,4 0 | 4,4 32 | 5,4 26 | 6,4 19 |
| 0,5 32 | 1,5 0 | 2,5 27 | 3,5 0 | 4,5 0 | 5,5 0 | 6,5 0 |
| 0,6 37 | 1,6 0 | 2,6 0 | 3,6 20 | 4,6 0 | 5,6 0 | 6,6 15 |
| 0,7 28 | 1,7 37 | 2,7 37 | 3,7 38 | 4,7 0 | 5,7 0 | 6,7 36 |

FIG. 17

Table VII
Pointer Array

| | | | | | | |
|---|---|---|---|---|---|---|
| 0,0<br>0 | 1,0<br>0 | 2,0<br>0 | 3,0<br>0 | 4,0<br>0 | 5,0<br>0 | 6,0<br>0 |
| 0,1<br>0 | 1,1<br>0 | 2,1<br>0 | 3,1<br>1 | 4,1<br>2 | 5,1<br>0 | 6,1<br>0 |
| 0,2<br>0 | 1,2<br>0 | 2,2<br>0 | 3,2<br>0 | 4,2<br>0 | 5,2<br>3 | 6,2<br>0 |
| 0,3<br>0 | 1,3<br>0 | 2,3<br>0 | 3,3<br>4 | 4,3<br>0 | 5,3<br>0 | 6,3<br>0 |
| 0,4<br>5 | 1,4<br>6 | 2,4<br>0 | 3,4<br>0 | 4,4<br>7 | 5,4<br>8 | 6,4<br>0 |
| 0,5<br>9 | 1,5<br>0 | 2,5<br>10 | 3,5<br>0 | 4,5<br>0 | 5,5<br>0 | 6,5<br>0 |
| 0,6<br>11 | 1,6<br>0 | 2,6<br>0 | 3,6<br>12 | 4,6<br>0 | 5,6<br>0 | 6,6<br>0 |
| 0,7<br>13 | 1,7<br>14 | 2,7<br>15 | 3,7<br>16 | 4,7<br>0 | 5,7<br>0 | 6,7<br>17 |

COMPUTER-IMPLEMENTED METHODS FOR ORGANIZING IMAGE DATA PRODUCED BY RESONANT MIE SCATTERING OF LIGHT FROM MICROPARTICLES AND RESULTING DATA STRUCTURES

CROSS-REFERENCE TO RELATED APPLICATION

This application claims priority under 35 U.S.C. §119 from U.S. Provisional Application Ser. No. 60/609,758, filed Sep. 14, 2004.

BACKGROUND OF THE INVENTION

1. Field of the Invention

The present invention relates to computer-implemented methods and computer readable storage media containing programs for organizing image data produced by resonant Mie Scattering of light from microparticles disposed in a free array, and to the resulting data structures produced therefrom.

2. Description of Related Art

Copending application WO 2004/044232, filed Nov. 6, 2003, Prober et al., titled "Microparticle-based Methods and Systems and Applications Thereof", assigned to the assignee of the present invention, discloses various methods, systems and applications that employ resonant light scattering as an analytical tool for determining a microparticle's identity as well as the presence and, optionally, the concentration, of one or more target analytes on the microparticle.

In general, a high refractive index microparticle is irradiated with light of a given wavelength and the microparticle scatters a portion of that light to a detector. As the incident wavelength is scanned, i.e., varied over an analytical wavelength range, a pattern or spectrum of scattered light as a function of wavelength results. The resonant light scattering spectra is detected by an imaging detector, such as a charge-coupled device (CCD) camera. The camera produces an electronic image of the particles at each wavelength step.

Thus, a complete wavelength scan results in a series of digital images of all the microparticle, one image for each wavelength interval in the scan. The intensity of scattering from a microparticle at a given wavelength is related to the brightness of that microparticle's scattering image at that wavelength. Computerized image processing and spectral analysis are required to obtain the complete scattering spectra of all the particles from the set of images obtained during the scan. Each particle has a distinct resonance light scattering pattern, due to natural processing variations, that can be used to identify the particle. The presence and optionally the concentration of a target analyte can be determined from the shift in the resonance light scattering pattern that occurs when the analyte binds to a capture probe immobilized on the surface of the particle. The magnitude of the shift is related to the concentration of the analyte in the solution.

Shown in FIG. 1 is a diagrammatic illustration of an image detection apparatus used to create images of scattered light from a plurality of microparticles 2 called a "free array". A population of the microparticles is isolated in an imaging optical cell 19 and, using a scanning diode laser 22 as a light source, imaged with a microscope 21. The microparticles could be randomly distributed or distributed in an ordered fashion such as in a tube or in a linear or rectangular array by constraining them in grooves, channels, or indentations on a substrate. The magnification is set to simultaneously image the particles of interest.

As the laser wavelength is increased through the wavelength range the microparticles are illuminated and a digital image is produced at each of a predetermined number ("Q") of wavelengths. The light scattered from microparticles in the field is collected and imaged by the objective lens 20 and associated optics of a camera 26. Illuminating wavelengths in the range of from about 770 nanometers to about 780 nanometers are particularly useful for the images under discussion. For a ten (10) nanometer range, a scan having using an illuminating laser having a "slew rate" (wavelength step, in nanometers per second) on the order of 0.2 results in a scan having a length of fifty (50) seconds. At an imaging rate on the order of thirty (30) images per second an experimental scan can produce about fifteen hundred images (Q=1500).

The camera 26 could be any imaging device capable of the speed and sensitivity required for this application. The camera 26 is preferably a digital camera having an electronic image plane based on a two-dimensional CCD (charge coupled device) or equivalent imaging means. The camera 26 thus produces an electronic image of the particles at each wavelength step (e.g., 0.2 nanometers per second). Preferably, the camera functions and data acquisition are controlled by a computer 10 operably linked to the camera 26 and to the scanning light source. The computer has software suitable for these purposes.

Each of the Q images produced by the digital camera 26 may be viewed on a video monitor 17 connected to the camera 26. Simultaneously, each image is captured by a suitable image capture card or other device 27 that functions to create (after appropriate analog-to-digital conversion) a digital representation of the electronic image on the electronic image plane of the camera. The digital image is stored in memory of the computer 10. A suitable image capture card is that sold by National Instruments Corporation as an IMAQ PCI 1428 image capture card.

A typical visual image taken at one given wavelength of polarized light from such a set of Q images is shown in FIG. 2. Light scattered by the mechanism of resonant Mie scattering emanates along the rim of a microparticle in the form of a substantially continuous (yet segmented) substantially circular rings. The incident and scattered light beams used to produce the visual and diagrammatic images of FIG. 2 were polarized independently, with the two axes of polarization parallel to each other. This results in sectors of scattered light centered approximately at the 12:00, 3:00, 6:00, and 9:00 positions of the substantially circular microparticle images.

As noted the intensity of resonant Mie scattering from a microparticle a given wavelength is related to the brightness of that particle's scattering image at that wavelength. This may be most graphically understood from FIGS. 3A through 3F, which are a series of stylized diagrammatic renderings of the visual image of FIG. 2 at respective illuminating wavelengths $L_1$ through $L_Q$. FIGS. 4A through 4F are a series of diagrams representing the images on the electronic image plane corresponding to each of the visual images. In FIGS. 4A through 4F the relative intensity values of the pixels are indicated by decimal numeric values.

As seen from close inspection of the renderings shown in FIGS. 3A through 3F and FIGS. 4A through 4F the intensity of the light scattered from the same given portion of the same microparticle changes over the wavelength scan. These intensity differences define a spectrum of scattered light as a function of wavelength for various locations on the microparticle. By monitoring changes in spectra over time and/or in the presence and optionally the concentration of a target analyte be obtained.

Each image of an entire viewed field (FIG. 2) or image of any selected region of interest therein (e.g., that portion bounded by the white border in FIG. 2) is typically in the shape of a rectangular or square matrix, or grid, as suggested in FIGS. 3 and 4. It should be appreciated, however, that the pixels in the image could be arranged to form other shapes on the image plane, such as a continuous or segmented annulus. Whatever its shape, the image contains a predetermined number ("N") of pixels.

For example, in a square image having length and width dimensions on the order of one thousand by a thousand (1000×1000) pixels, the total number N of pixels in an image (whether the "image" is defined as the entire field or a selected region of interest of a field) could be on the order of one million (1,000,000). When one considers that in a typical experimental scan approximately fifteen hundred images may be produced (i.e., Q=1500) the data storage requirements (assuming at least ten-bit digital accuracy) for the complete set of such digital representations of the Q images from this single experiment could be on the order of three (3) gigabytes.

Handling this prodigious amount of data and retrieving selected portions of this data for processing purposes (e.g., for effecting analysis of the microparticles) is problematic. In addition, the mere storage of such a vast amount of data presents issues of considerable difficulty.

Accordingly, in view of the foregoing it is believed advantageous to provide methods and programs for organizing the image data produced by the scattering of light (particularly resonant Mie scattering) from microparticles disposed in a free array that make the handling and retrieval of information for display, analysis or other purposes more rapid and more efficient. It is believed to be of further advantage if such data organization methods result in a more compact and manageable amounts of data, thus reducing significantly the data storage requirements for free array testing.

SUMMARY OF THE INVENTION

The present invention is directed to computer-implemented methods and programs for organizing image data representing light scattered from one or more substantially spherical microparticles and the data structures resulting therefrom.

In one embodiment the present invention includes the creation of a digital representation of an image produced on an electronic image plane by light scattered from one or more substantially spherical microparticles at each of a predetermined number (Q) of illuminating wavelengths, each of the Q images having a predetermined number (N) of pixels. For each of the N pixels, an associated Image Intensity Data Array containing Q values is created. The Q values in at least some of the data arrays denote the intensity of light at each of the Q wavelengths scattered from a location on a microparticle corresponding to the pixel associated with the data array. A Composite Image Array having N values is also created. Each value in the Composite Image Array is based upon and is generated using a corresponding Image Intensity Data Array. The values in the Composite Image Array may be based upon the maximum intensity value in the corresponding Image Intensity Data Array. Alternatively, the values in the Composite Image Array may be based upon the difference between the maximum and minimum intensity values in the corresponding Image Intensity Data Array The data structure resulting from this first embodiment of the invention includes a collection of N Pixel Records where each Pixel Record is associated with one pixel. The collection of Pixel Records is inclusive, in the sense that the Pixel Record from each pixel in the image is included within the data structure. The Pixel Records are arranged sequentially in a linear array in accordance with the raster order. Each Pixel Record has a Record Header and an Image Intensity Data Array. Each Image Intensity Data Array contains Q values. At least some of the data arrays denotes the intensity of light at each of the Q wavelengths scattered from a location on a microparticle corresponding to the pixel associated with the data array. The Record Header in each Pixel Record contains information specifying the location on the electronic image plane of the pixel associated with the Image Intensity Data Array.

In accordance with a second embodiment of the present invention, the digital representation of the Q images and the Image Intensity Data Array associated each with the N pixels in each image is created. From the N Image Intensity Data Arrays, a select set of S number of Image Intensity Data Arrays is created. Each Image Intensity Data Array in the select set has at least one intensity value that exceeds a predetermined analog threshold. A Pointer Array containing N values is also created. The Pointer Array correlates the position on the electronic image plane of the pixel associated with each Image Intensity Data Array in the select set with the order of selection of that data array into the select set.

The data structure resulting from this second embodiment of the present invention includes only the S selected Pixel Records whose image intensity data arrays have at least one value exceeding the analog threshold. The Pixel Records are arranged sequentially in a linear array in accordance with the raster order. The data structure may also include the Pointer Array, the Composite Image Array, and a Composite Thresholded Image Array.

BRIEF DESCRIPTION OF THE DRAWINGS

The invention will be more fully understood from the following detailed description taken in connection with the accompanying drawings, which form a part of this application and in which:

FIGS. 3A through 3F are a series of stylized diagrammatic renderings of the visual representation of the image of FIG. 2 at respective selected illuminating wavelengths $L_1$ through $L_Q$;

FIGS. 4A through 4F are representations of the images on the electronic image plane (e.g., camera) respectively corresponding to each of the visual representations shown in FIGS. 3A through 3F, wherein each decimal numeric value in each of pixel location shown in FIGS. 4A through 4F quantifies the intensity of the scattered radiation as visually indicated in corresponding pixels on respective visual images of FIGS. 3A through 3F;

FIGS. 7A and 7B contain Table I, which is a tabular representation of a plurality of Image Intensity Data Array in the Pixel Records for an inclusive ("P-1") pixel stack, each Image Intensity Data Array corresponding to a pixel in the electronic image;

FIG. 8 is a graphical representation of a data structure comprising the collection of Pixel Records for an inclusive ("P-1") pixel stack as tabulated in FIGS. 7A and 7B;

FIG. 9 contains Table II, which is a tabular representation of a Composite Maximum Image Array derived from the plurality of Pixel Records for an inclusive ("P-1") pixel stack;

FIG. 10 contains Table III, which is a tabular representation of a Composite Minimum Image Array derived from the plurality of Pixel Records for an inclusive ("P-1") pixel stack;

FIG. 11 contains Table IV, which is a tabular representation of a Composite Average Image Array derived from the plurality of Pixel Records for an inclusive ("P-1") pixel stack;

FIG. 14 contains Table V, which is a tabular representation of a plurality of Image Intensity Data Array in the Pixel Records for a Threshold ("P-2") pixel stack;

FIG. 16 contains Table VI, which is a tabular representation of a Composite Threshold Image Array for a Threshold ("P-2") pixel stack;

FIG. 17 contains Table VII, which is a tabular representation of a Pointer Array used in conjunction with the Composite Threshold Image Array of FIG. 16.

Figure 1:
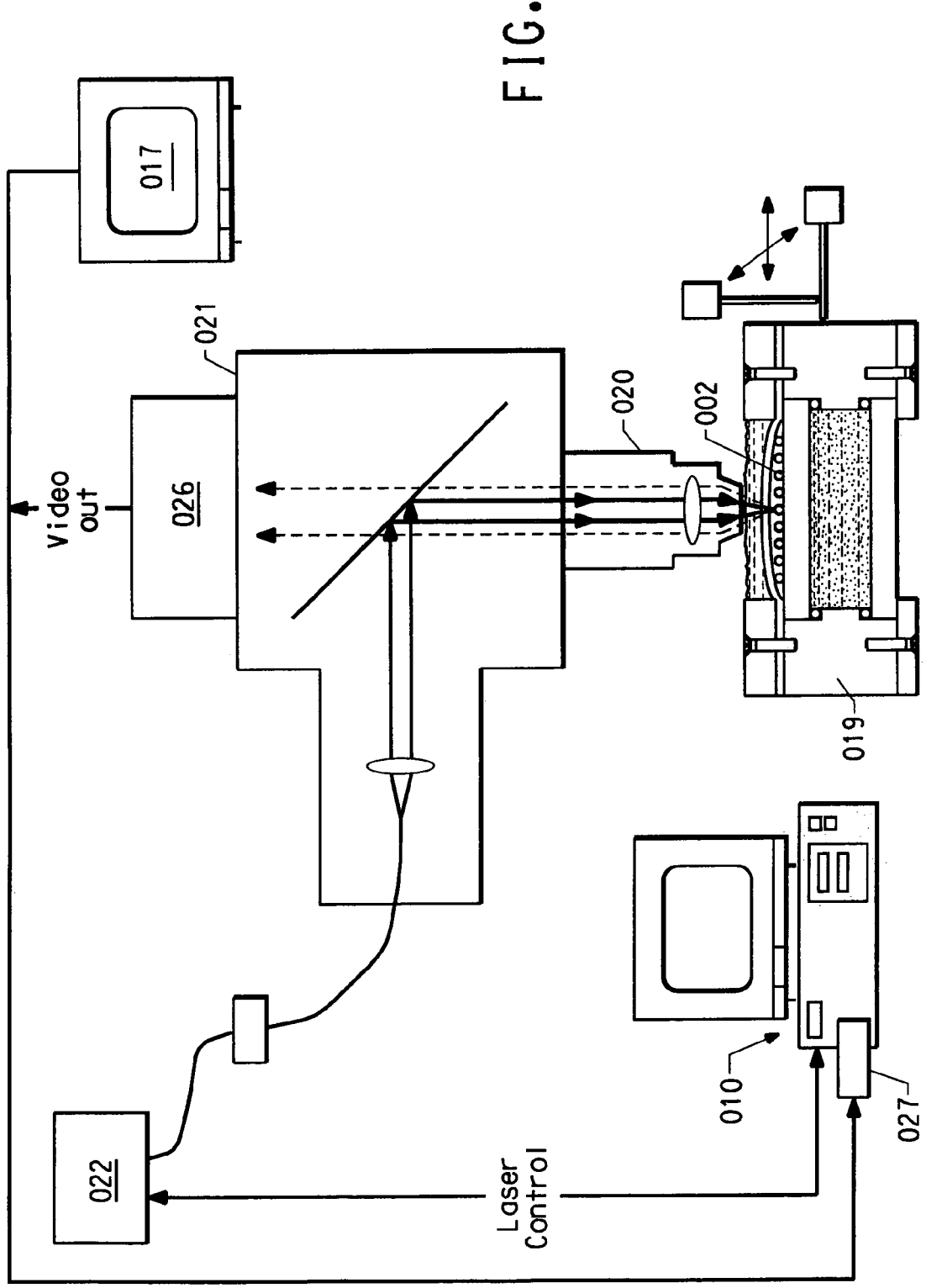
FIG. 1 is a stylized diagrammatic illustration of an image detection apparatus used to create images of scattered light from a multiplicity of microparticles disposed in a free array.

A Program Appendix, pages 27 through 29, forming part of the specification of this application is positioned at the end of the description but before the claims.

DETAILED DESCRIPTION OF THE INVENTION

Throughout the following detailed description (including the Appendix), similar reference characters refer to similar elements in all Figures of the drawings.

In the way of general comments, as is noted in the Background, FIGS. 4A through 4F are representations of the electronic image plane of the camera 26. The image plane has a width dimension ("W") extending in the positive X-direction of seven (7) pixels (0, 1, 2, . . . 6) and a height dimension ("H") extending in the positive Y-direction of eight (8) pixels (0, 1, 2, . . . 7). The decimal numeric value in each of the pixel locations shown in these Figures numerically quantifies the intensity of the scattered radiation that is visually depicted in corresponding pixels on respective visual images of FIGS. 3A through 3F.

The visual and numeric renderings of FIGS. 3 and 4 are presented to facilitate an understanding of the operation of the various aspects of the present invention. However, it will be appreciated that it is the digital representations of the image values as stored in binary format in a computer memory that are retrieved and operated upon using the computer implemented techniques of the present invention.

Figure 2:
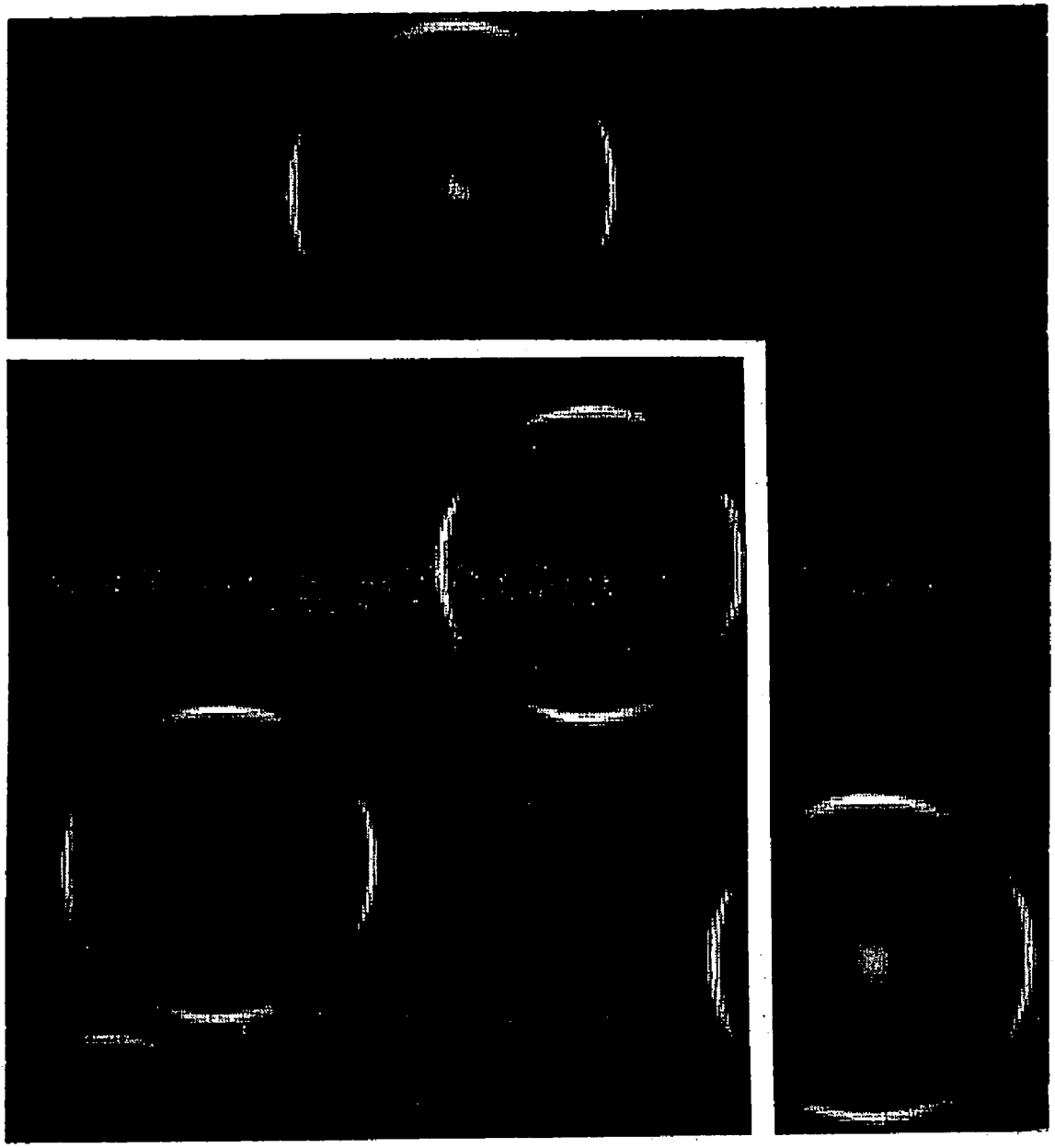
FIG. 2 is a digital image of scattered polarized light from a group of microparticles in a field of a predetermined size acquired using the image detection apparatus of FIG. 1 at a single wavelength of incident polarized light.
Figure 3B:
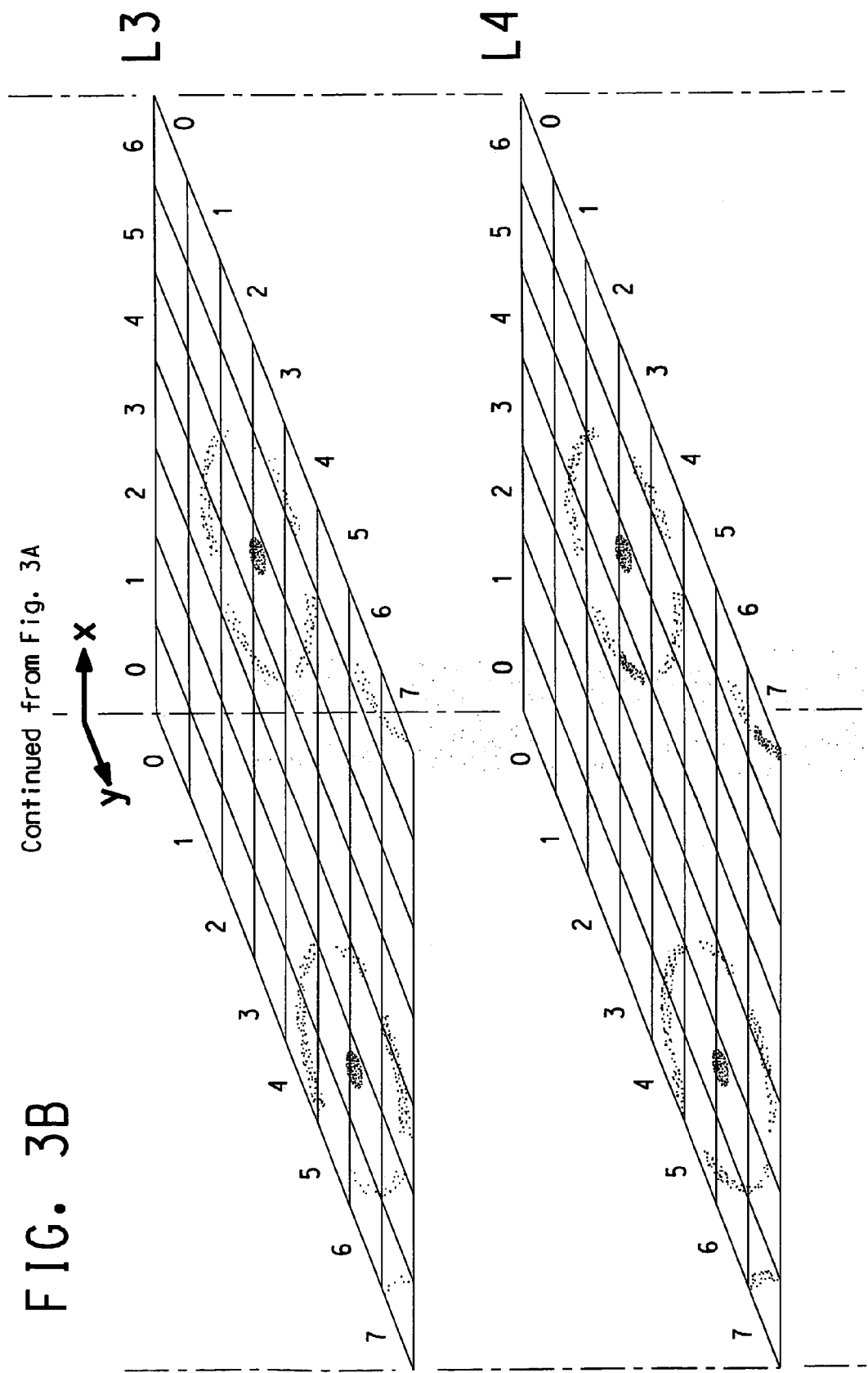
Figure 3C:
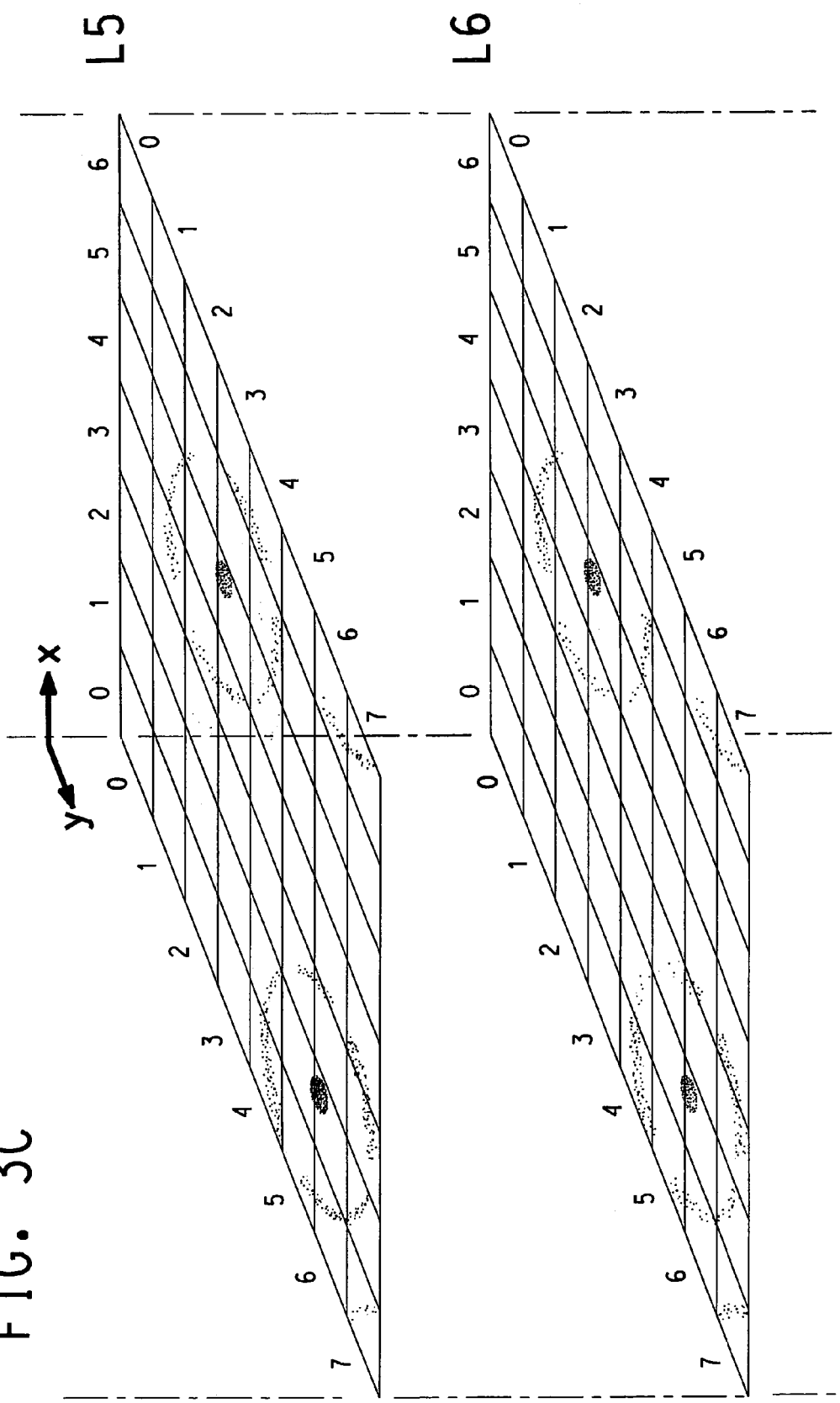
Figure 3D:
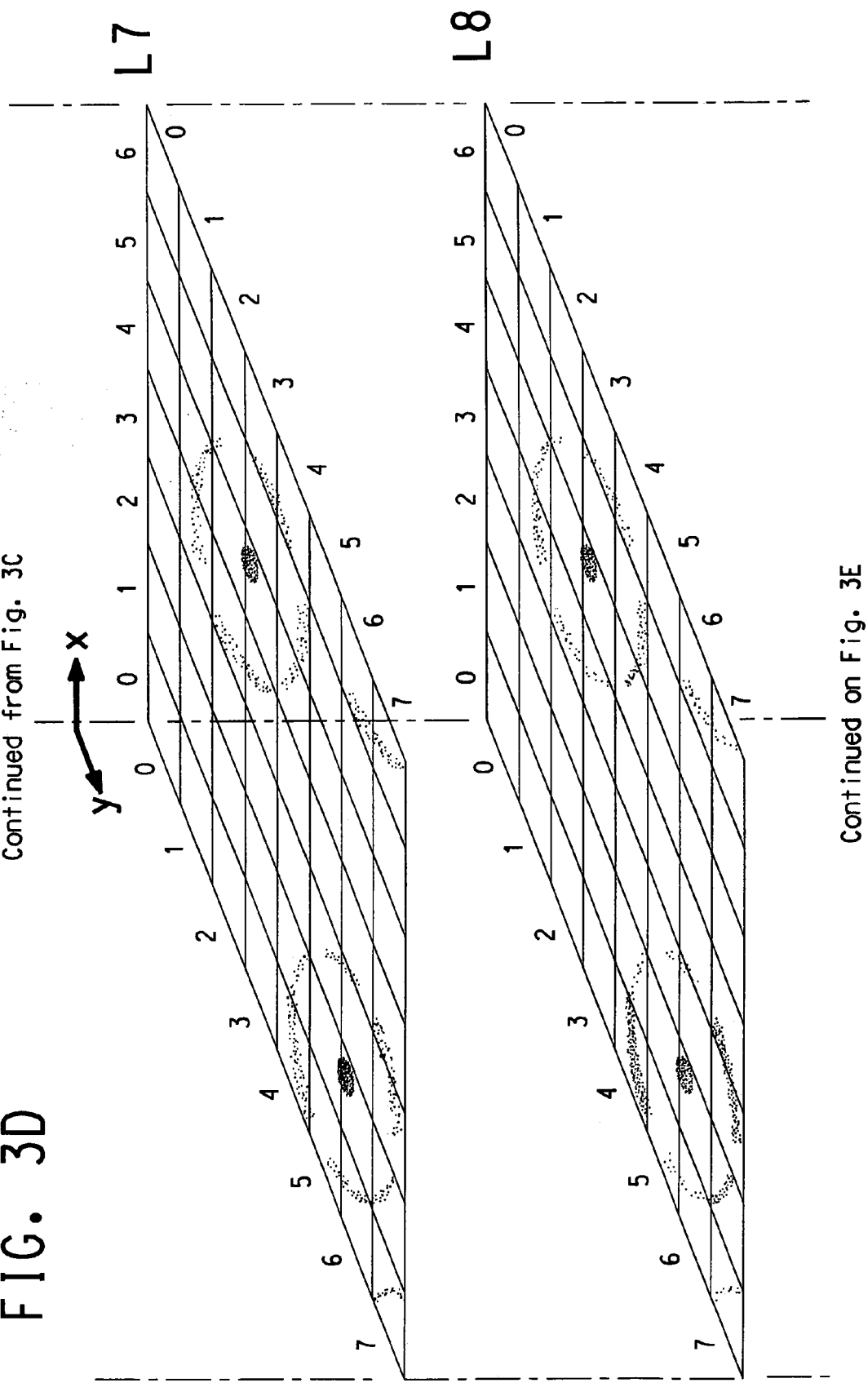
Figure 3E:
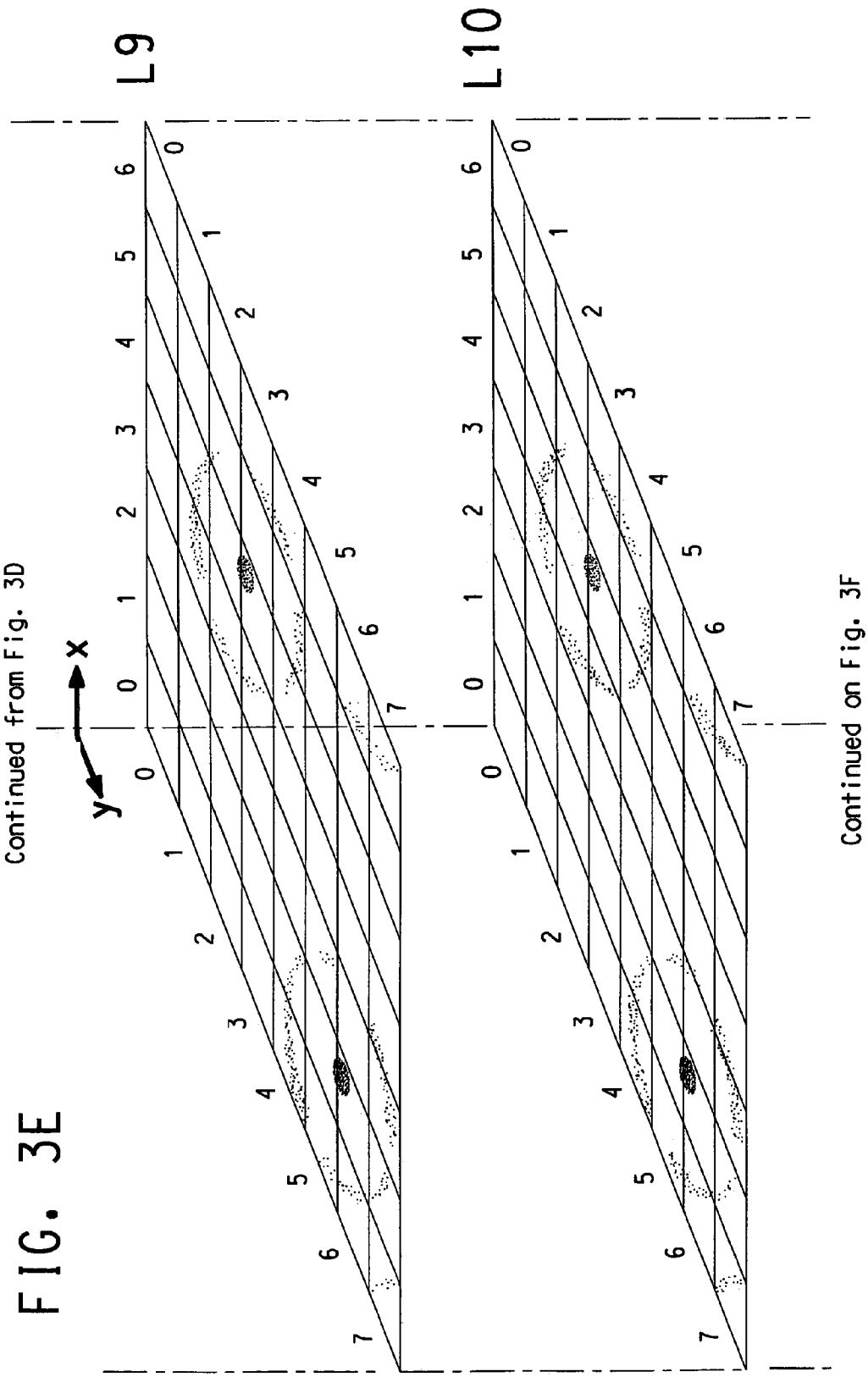
Figure 4B:
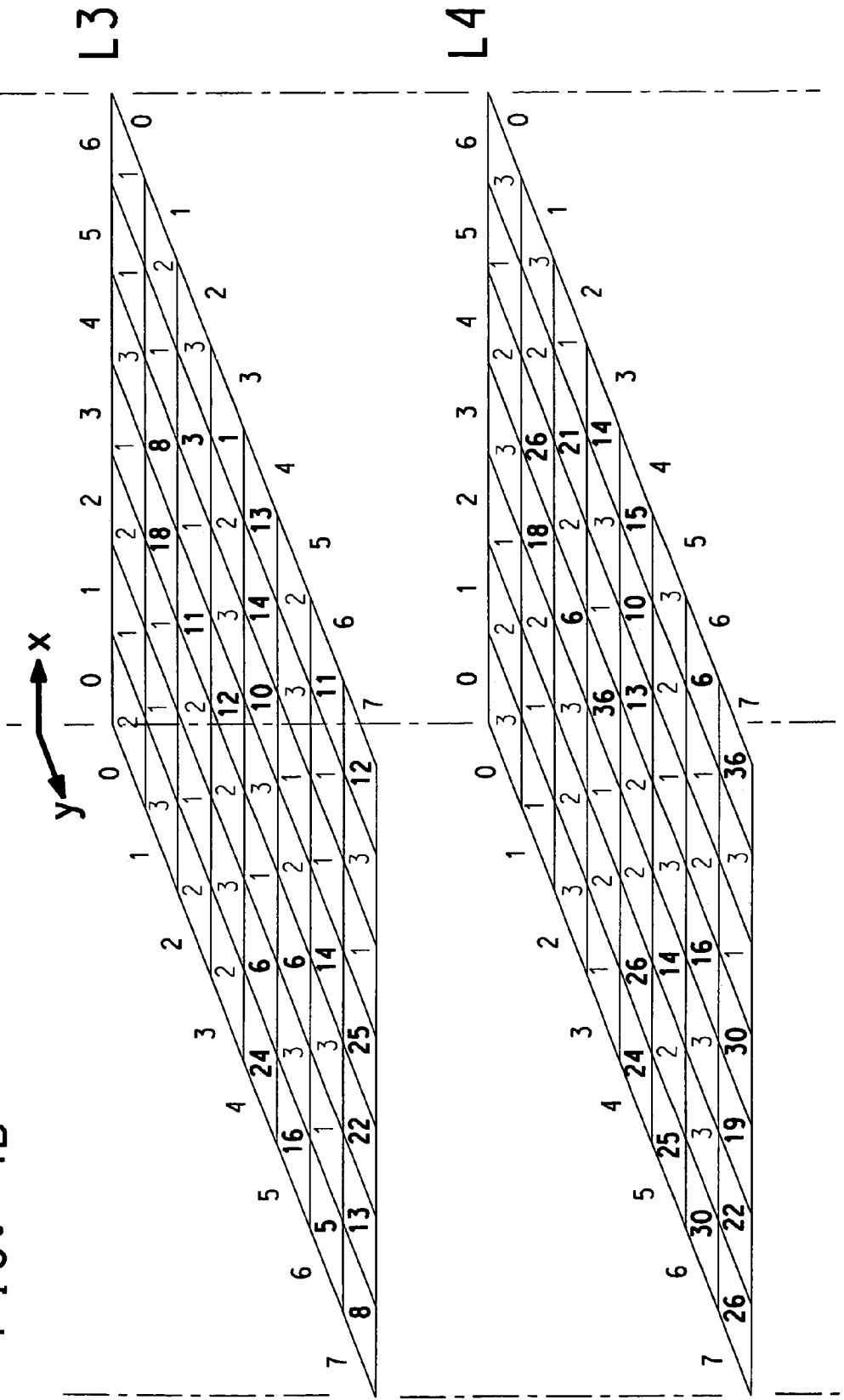
Figure 4C:
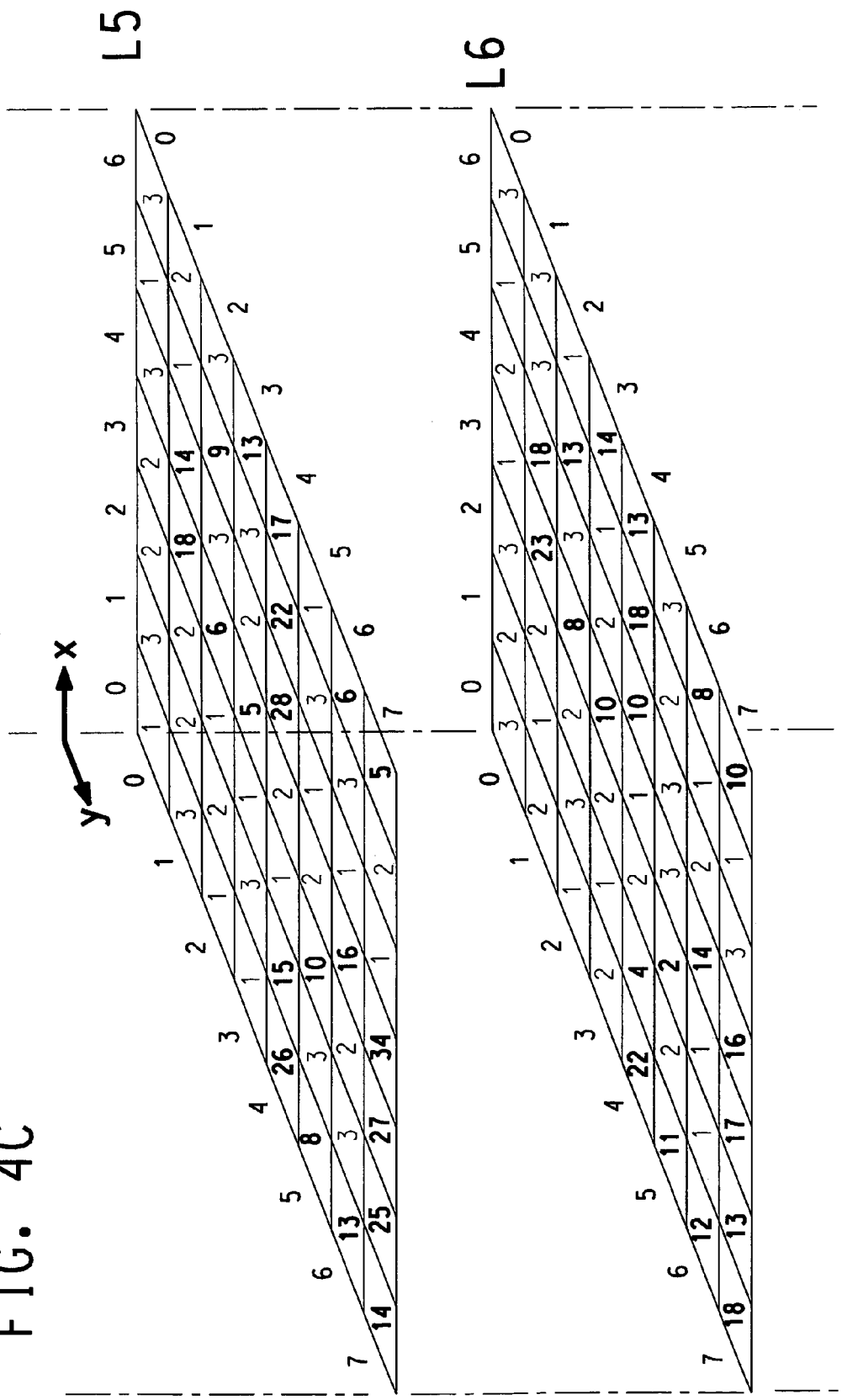
Figure 4D:
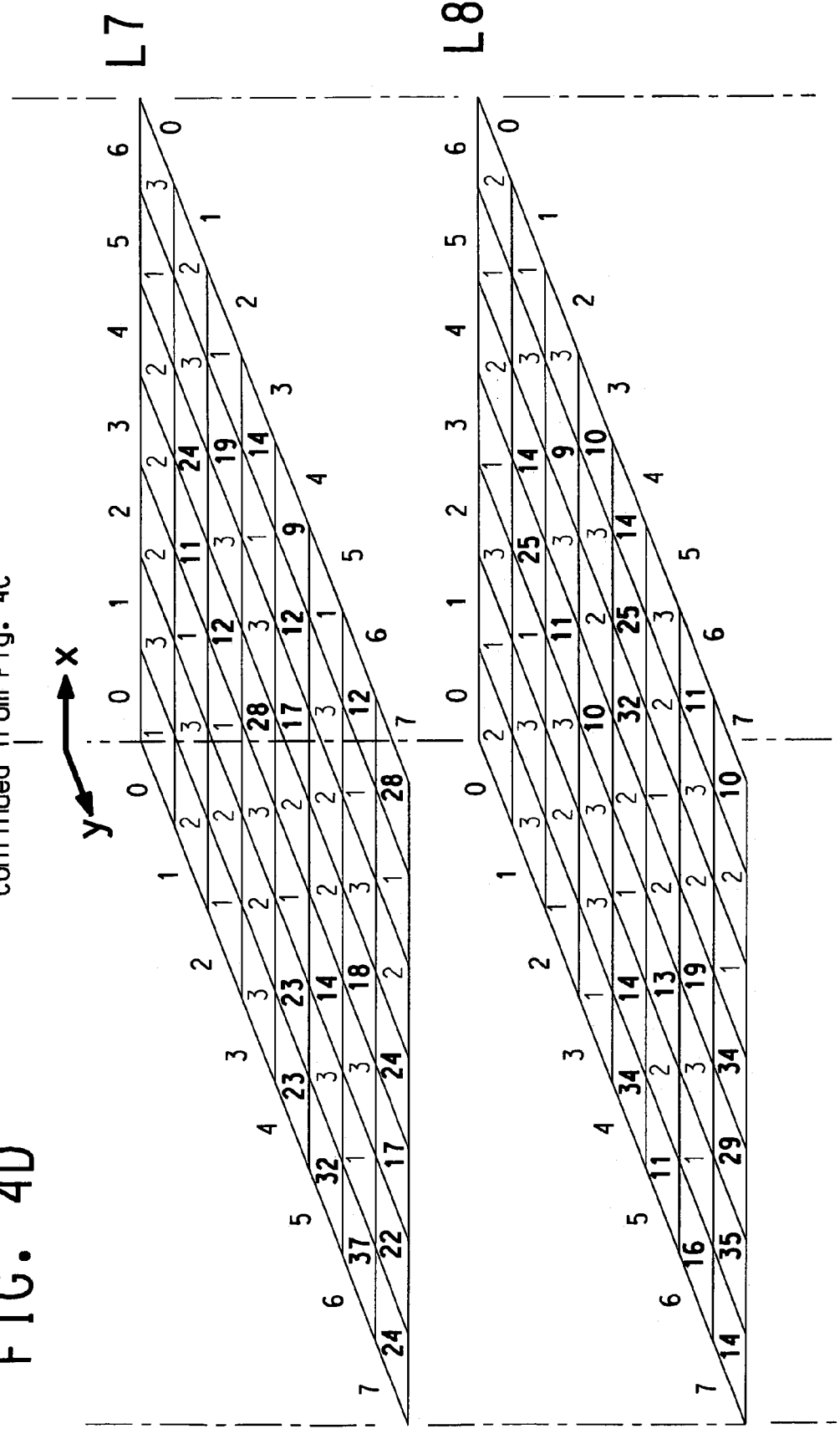
Figure 4F:
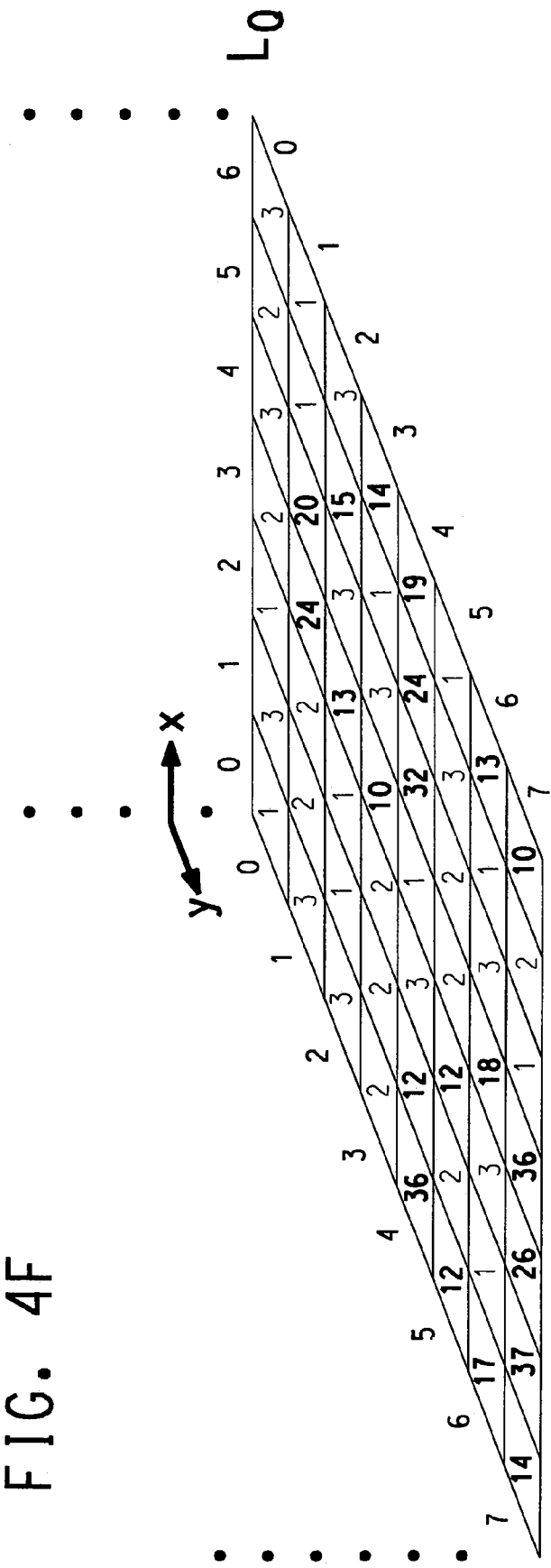

It is noted that only that region of interest of FIG. 2 bounded within the white border thereon is used to define the visual and numeric "image" respectively represented in FIGS. 3 and 4. It may thus appreciated that the methods of the present invention may be practiced on an "image" of any size, including the "image" of any region of interest selected from a larger field of view. Moreover, although the "image" is typically represented in the form of a square or rectangular matrix of picture elements, it is within the contemplation of the present invention to define a region of interest and an image representative thereof that exhibits other shapes, e.g., a continuous or segmented annulus.

The resolution of the camera 26 determines the number of pixels in an "image" under consideration, whether that image is of the entire field or a selected region of interest therein. The higher the resolution of the camera, the greater is the number of pixels in a given "image". Thus, it should be appreciated that the character "N", when used to refer to the number of pixels in an image, is not intended to denote one single predetermined value, but instead to refer to that number of pixels produced by the camera generating the "image" under discussion.

Depending upon the positions of the microparticles within the imaging cell at least some of the pixels in an image correspond to a respective physical location on a microparticle. Moreover, since during a scan the microparticles do not move with respect to their substrate, the same pixel in each image corresponds to the same location on the same microparticle. Thus, on any given image in a set of Q images, the intensity value of these pixels denotes the intensity of the light radiation at one of the Q wavelengths scattered from a physical location on a microparticle. The intensity values in the others of the pixels in the image are generated from light scattered or reflected from other features on the imaging cell or on the substrate for the microparticles.

In the typical instance images generated on the electronic image plane of the camera 26 are digitally captured and operated upon using the methods of the present invention substantially simultaneously with the occurrence of the scans of the microparticles (i. e, in real time). However, it should be understood that the creation of an image on the electronic image plane and its digital capture and the operations using the present invention need not occur in real time. It lies within the contemplation of the present invention to capture digital images created on an electronic image plane at one point in time and to operate on those digital images using the methods of the present invention at a later point in time.

-o-O-o-

The image data organization techniques provided by the methods and programs of the present invention and the data structures resulting therefrom are useful both to organize more efficiently image data for further handling and processing as well as to reduce the requirements for storage of image information while in memory of the computer 10 or when archived off-line.

Figure 5:
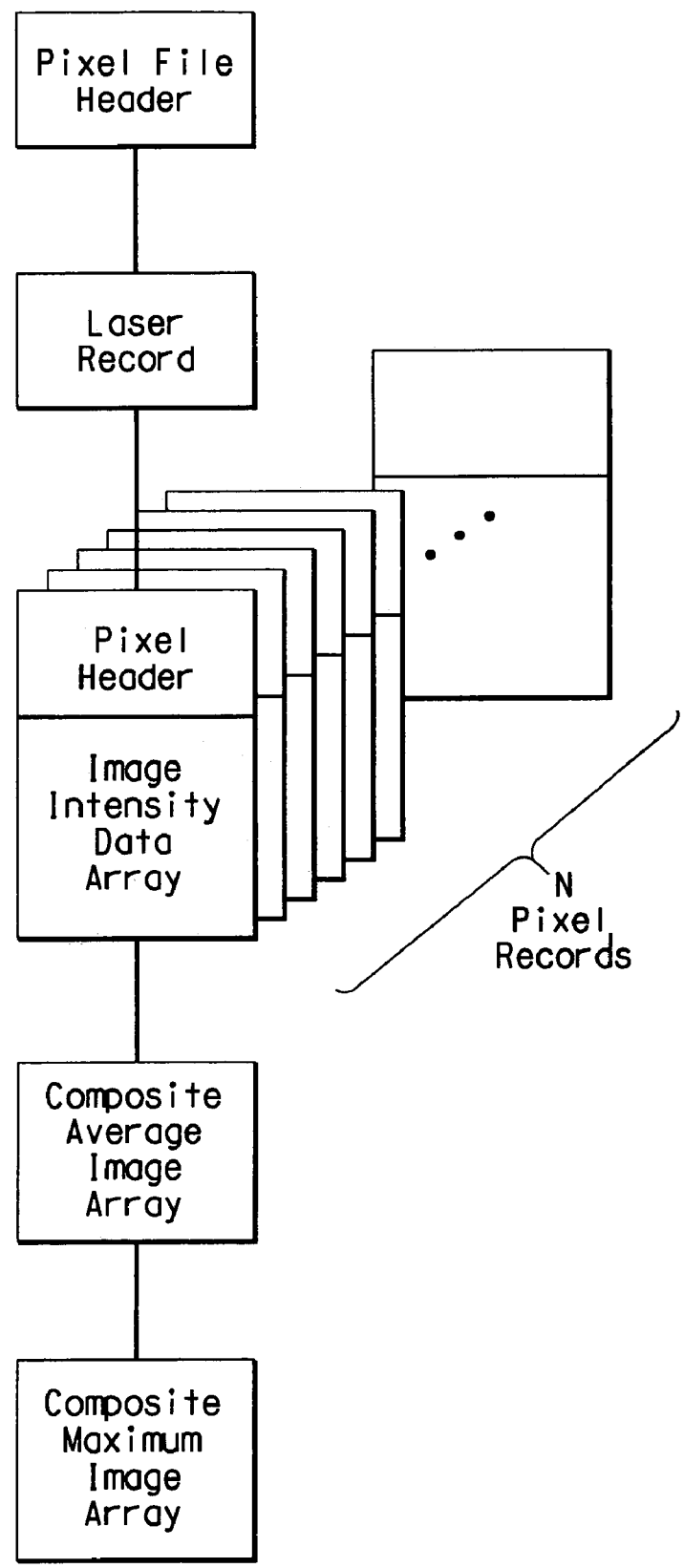
FIG. 5 is a diagrammatic representation of the organization of the data structure formed in the implementation of an inclusive ("P-1") pixel stack in accordance with the present invention.

THE INCLUSIVE ("P-1") PIXEL STACK The first data organization discussed is the Inclusive Pixel Stack, also termed a "P-1 Stack". The Inclusive Pixel Stack is a data record that includes intensity information from all of the pixels in an image. A diagrammatic representation of the Inclusive Pixel Stack is shown in FIG. 5.

The Inclusive Pixel Stack includes a Pixel File Header file, an illuminating laser record, a collection of Pixel Records derived from each of the pixels in all of the images taken during a scan, and various composite data arrays of the intensity information.

Figures 6A, 6B:
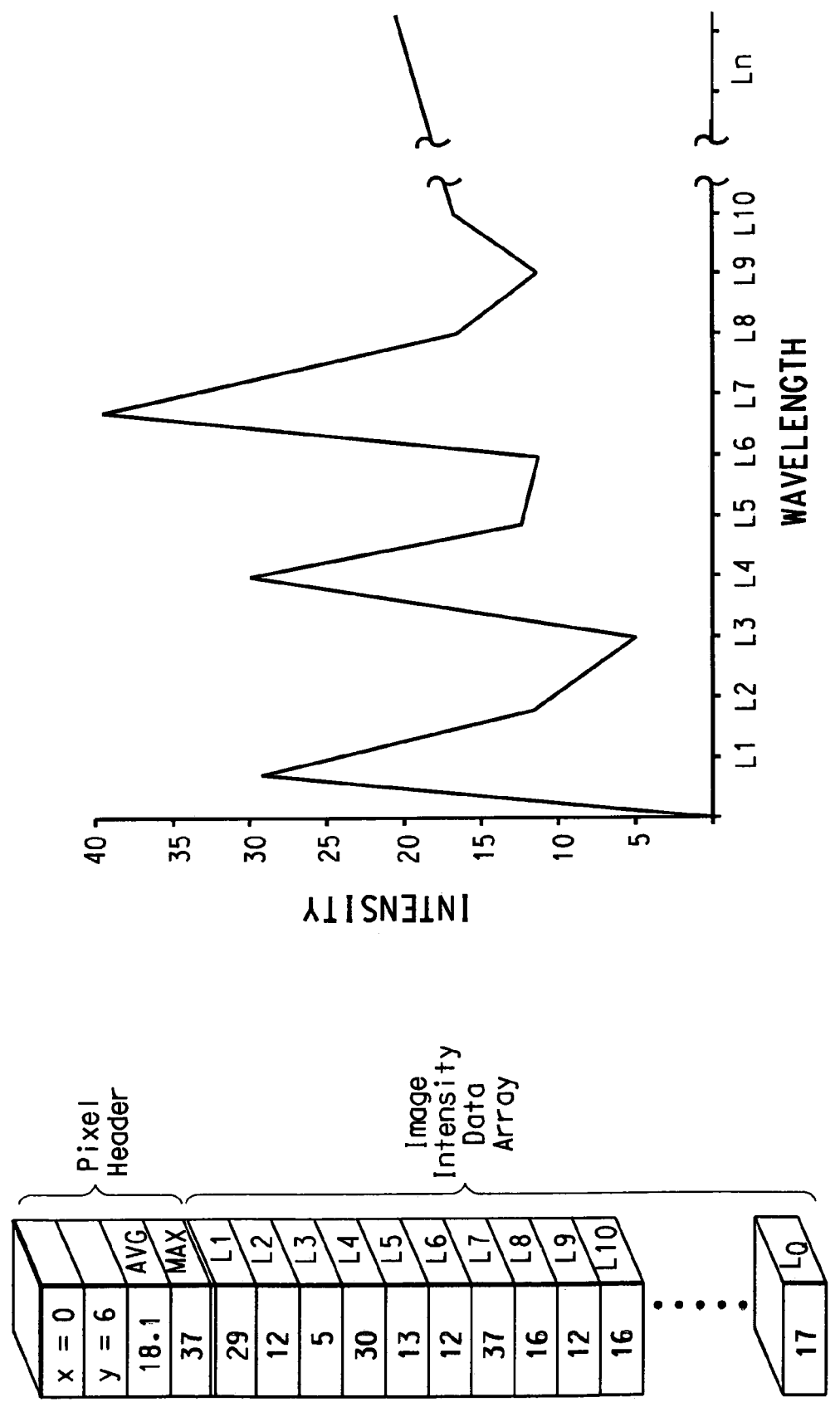
FIG. 6A is a diagrammatic representation of an individual Pixel Record in an inclusive ("P-1") pixel stack.
FIG. 6B is a graphical representation of the spectrum contained in the Image Intensity Data Array of the Pixel Record shown in FIG. 6A.

Pixel Record A Pixel Record is a data structure associated with a pixel. A Pixel Record comprises a Pixel Header and an Image Intensity Data Array. FIG. 6A is a graphical representation of a Pixel Record for the pixel (0,6) illustrated in the renderings of FIGS. 3 and 4.

An Image Intensity Data Array is a file organized as a (Q×1) linear array (string) containing Q values, where each value represents the intensity of the radiation at one of the Q wavelengths detected on the electronic image plane.

The Q values in at least some of the data arrays denote the intensity of light at each of the Q wavelengths scattered from a location on a microparticle corresponding to the pixel associated with the data array. As seen from FIG. 6A the sequential values stored in the Image Intensity Data Array are a tabulation of the intensity value for the same pixel (0,6) in FIGS. 4A through 4F. These values are, in turn, representative of light scattered, as by resonant Mie scattering, from the same portion of the microparticle illustrated in FIGS. 3A through 3F.

Graphically, as suggested in FIG. 6A, the Image Intensity Data Array for a given pixel may be envisioned as a tower of blocks. Proceeding sequentially from top to bottom each block holds information regarding the intensity of light incident on that pixel at a changing (i.e., an increasing or decreasing) wavelength. The Image Intensity Data Array for each pixel thus defines the spectrum of scattered light from the portion of the microparticle corresponding to that pixel. A plot of the image intensity as a function of illuminating wavelength yields the distinct resonance light scattering spectrum produced by that portion of the microparticle. FIG. 6B illustrates the spectrum of the portion of the microparticle producing the Image Intensity Data Array of FIG. 6A.

The Pixel Header is attached to each Image Intensity Data Array. The pixel header contains the X and Y coordinates of the pixel from which the Image Intensity Data Array is derived, as well as intensity information, such as the average image intensity value, the maximum image intensity value, and the difference between the maximum and the minimum intensity values.

As noted, not all Image Intensity Data Arrays represent light scattered from a portion of a microparticle. For example, inspection of FIGS. 3A through 3F indicates that no microparticle is physically present in that portion of the image plane corresponding to pixel (6,2). However, extraneous reflection or scattered have produced detectable intensities on the image plane at that pixel location, as indicated in FIGS. 4A through 4F.

In a P-1 Stack an Image Intensity Data Array is created for each pixel in the electronic image. Thus, if the visual and electronic images each contain N pixels, there is a corresponding number N of Image Intensity Data Arrays.

FIGS. 7A and 7B show Table I, which is a tabular representation of the plurality of Image Intensity Data Arrays derived from the electronic images of FIGS. 4A through 4F. The columns of Table I are arranged across the sheet of drawings in raster fashion, moving across the X axis (image Width) for each value along the Y axis (image Height). The numeric values in each column denote the intensity of the light at one of the Q wavelengths detected on the electronic image plane, whether the detected light is scattered from a microparticle or from another feature. In the creation of the P-1 Stack no determination is made as to whether the detected intensity is derived from a portion of a microparticle or from an extraneous or background source.

Of course, the Image Intensity Data Arrays of most particular interest are the arrays for those pixels that correspond to a portion of a microparticle. As appreciated from FIGS. 3A through 3F the data arrays corresponding to pixels having the following respective (X,Y) coordinates are especially noteworthy and are indicated in boldface type:

(3,1) (4,1);
(3,2) (5,2);
(3,3) (6,3);
(0,4) (1,4) (4,4) (5,4) (6,4);
(0,5) (2,5);
(0,6) (3,6);
(0,7) (1,7) (2,7) (3,7) (6,7).

As can be verified by inspection of FIGS. 4A through 4F each of the values in the these Image Intensity Data Arrays denotes the intensity of the light at one of the Q wavelengths scattered from that location on a microparticle corresponding to the pixel.

In the data structure of the inclusive P-1 Stack the collection of Pixel Records are arranged as a linear array of linear arrays of data (i.e., a string of strings). FIGS. 8A and 8B comprise a graphical representation of a data structure comprising the collection of Pixel Records for the inclusive ("P-1") pixel stack as tabulated in FIGS. 7A and 7B.

Composite Image Arrays Also included within the P-1 Stack are various composite arrays of intensity data, referred to herein as "Composite Image Array(s)". These arrays are organized as multi-dimensional arrays that mirror the layout of the pixels in the image plane. The Composite Image Array has N values, each value in the Composite Image Array being generated using a corresponding Image Intensity Data Array. The values in the Composite Image Array are based upon the pixel intensities in the Intensity Data Array and may be generated from the corresponding Image Intensity Data Array in various ways, such as: using the maximum intensity values to produce a Composite Maximum Image Array; or calculating the average intensity values to produce a Composite Average Image Array, both as described below. The values in the Composite Image Array may alternatively be generated by calculating the difference between the maximum and minimum intensity values to produce a Composite Difference Image Array The values in the Composite Image Array may alternatively be generated in still other ways, including, but not limited to: calculating the median intensity values to produce a Composite Median Image Array; calculating the square of the intensity values to produce a Composite Squared Image Array; calculating the logarithm of the intensity values to produce a Composite Logarithmic Image Array; calculating the ratio of the maximum to minimum intensity values to produce a Composite Ratio Image Array; calculating the difference between the maximum and minimum intensity values divided by the maximum intensity values to produce a Composite Difference Ratio Image Array; or using the minimum intensity values to produce a Composite Minimum Image Array.

Among the various useful arrays included in the P-1 Stack are the Composite Maximum Image Array and the Composite Average Image Array. The Composite Difference Image Array and the Composite Minimum Image Array may also be generated and included in the P-1 Stack. All of these composite arrays are useful in connection with the various methods for analyzing microparticles using the scattered light images.

By way of representative example, a tabular representation of the Composite Maximum Image Array is given by Table II in FIG. 9. This array contains the maximum intensity value from each Image Intensity Data Array. The numeric values in the Composite Maximum Image Array denote the maximum intensity of light scattered from the location on a microparticle corresponding to the pixel.

By way of other representative examples, a tabular representation of the Composite Minimum Image Array and the Composite Average Image Array is given by Tables III and IV in FIGS. 10 and 11, respectively. As their names indicate the numeric values in these arrays denote either the minimum or the average intensity of light scattered from the location on a microparticle corresponding to the pixel, as the case may be. Specific examples of other possible Composite Image Arrays may be readily generated.

It should be noted that the term "image" as used in this application in connection with the names of these arrays is meant to convey the idea that the data contained within these arrays can be used to render visual images illustrating features of the data. For example, the values in the Composite Maximum Image Array can be used to render a visual image of the maximum intensity of light detected at each individual pixel on the image plane. Of particular interest in such a composite image would be the representation of maximum intensity of light scattered from the pixels corresponding to locations on a microparticle.

Pixel File Header The Pixel File Header is a record located at the head of the P-1 Stack containing pertinent information regarding the scan to which the stack relates. Typically, the Pixel File Header should include at least the highest and lowest image intensity values derived from all of the Q images in the scan.

Other types of information that could also be contained in the Pixel File Header include the number and types of images in the scan, the Width and Height of each of the images produced, and/or the researcher conducting the scan. In general, the Pixel File Header could include any information that would assist in making the Pixel Stack as complete an archive as is desired concerning a particular scan.

Laser Record The P-1 Stack may also include a Laser Record containing information regarding the illuminating laser light source. Typical examples of information included within the Laser Record would be the slew rate, the initial and final wavelength values, information relating to laser power, and/or laser etalon, which relates details regarding the laser power controller.

Program Listing A pseudocode listing of a program by which a P-1 Stack is created is set forth on page A-1 of the Appendix. References in the following discussion are keyed to the corresponding line numbers in the pseudocode listing.

The Width of each image is indicated in the listing by the variable "W", while the Height of each image is indicated in the listing by the variable "H".

The binary "P-1 Stack" file is opened on disk (or other medium) in Line 1.

The files "PixelFileHeader" and "LaserRecord" are created on the disk in Lines 2, 3.

The array "Image Intensity Data Array" is dimensioned as a (Q×1) array [i.e., from subscripts "0" to "(Q−1)"] in Line 4.

In Lines 5 and 6 the arrays "Composite Maximum Image Array" and "Composite Average Image Array" are each dimensioned as a (W×H) array [i.e., in the Width dimension from subscripts "0" to "(W−1)" and in the Height dimension from subscripts "0" to "(H−1)"].

Initial Values in the buffers "LowestPixelValue" and "HighestPixelValue" are set in Lines 7 and 8. The initial value for the "HighestPixelValue" is zero. The initial value for the "LowestPixelValue" is any predetermined number larger than any expected intensity value.

The Y values of the pixel locations are looped in an outer loop from Lines 9 to 30. For each Y value, the X values of the pixel locations are incremented in a first nested inner loop from Lines 10 to 29.

Within the "X" loop, for each "X" value, the "X" and "Y" information in the Pixel Header record is set Lines 11 and 12.

In Line 13 a call is made to a utility referred to as "GetPixel", which functions to retrieve pixel intensity values from the store of digital image representation ("MyImages") and to place those values into the array "Image Intensity Data Array". The utility "GetPixel" is provided with the number of images ("Q"), the number of bytes of intensity information per pixel, and the Width of the image ("W"). With this information in hand the utility "GetPixel" reads through the stored digital images and, starting at the first stored image location ["MyImages(0)"] sequentially takes the intensity value at the then-current X and Y pixel location on each of the Q images. The utility places the intensity value in the array "Image Intensity Data Array", starting with the first position in that array [i.e., "Image Intensity Data Array(0)"]

The buffers "Sum" and "Max" are initialized to zero (Lines 14 and 15).

For each X value within the "X" loop, a nested loop (Lines 16 to 22) sequentially reads the array "Image Intensity Data Array" through all of Q values [0 to (Q−1)].

On each iteration through the Q values several things occur, viz.:
the buffer "Sum" is increased by the then-current Pixel Value (Line 18);
the then-current Pixel Value is compared to the current value in the Max buffer. If the comparison is "True" the value in the Max buffer is changed to the current value (Line 19);
the then-current Pixel value is also compared to the current LowestPixelValue and HighestPixelValue in these buffers (Lines 20 and 21). If either comparison is "True" the value in the appropriate buffer is changed.

Both the average pixel value ("AvgPixel" equal to "Sum" divided by the number of images Q) and the maximum pixel value ("MaxPixel") are entered into the Pixel header (Lines 23 and 24). These same values are also loaded into the then-current (X, Y) pixel location in both the "Composite Average Image Array" and the "Composite Maximum Image Array" (Lines 25, 26).

The Pixel Header and the "Image Intensity Data Array" for then-current (X, Y) pixel location is saved (Lines 27, 28).

The X value is then incremented (Line 29) and the "X" loop (Lines 10 to 29 iteratively repeated for each updated then-current (X,Y).

After all X looping is complete, the Y value is incremented (Line 32) and the full "Y" loop (Lines 9 to 30) iteratively repeated for all values of Y.

At the completion of the Y loop:
the "Image Intensity Data Array" for each pixel location has been created and stored to disk (each iteration of Line 28);
both the "Composite Average Image Array" and "Composite Maximum Image Array" derived from all of the Q images have been created and stored to disk (Lines 31, 32); and
both the Lowest Pixel Value and the Highest Pixel Value present in all of the Q images have been identified, and entered in the "Pixel File Header" (Lines 34, 35).

The full, finished "Pixel File Header" is sent to disk for storage (Line 35) and the P-1 Stack closed (Line 36).

Advantages of the P-1 Stack The organization of the P-1 Stack offers several advantages.

The information is saved in binary format, the most efficient storage format.

Storing image intensity data in a data structure comprising a string of pixel records, where each Pixel Record is itself a string of intensity values, facilitates retrieval of intensity information for any given pixel.

Each pixel in the string of Pixel Records has a Record Number ("R") that is defined by the (X,Y) coordinates of that pixel taken in view of the Width ("W") and Height ("H") of the image. For any given pixel having the coordinates (X,Y) the Record Number ("R") is given by the formula:

$$R=(Y \cdot W)+X+1$$

Knowing the Record Number ("R"), the number of images (Q), and the number of bytes of memory ("B") accorded to each image intensity value, the position of that Pixel Record (as measured from the beginning of the collection of Pixel Records in the P-1 Stack) is determined by the relationship:

$$Position=(R-1) \cdot (Q) \cdot (B)$$

[with at least ten-bit digital accuracy there are two bytes accorded to each image intensity value (i.e., B=2)].

The Position defines the starting location from which an intensity record (Q images, each with B bytes) is read. Knowing the Position of the Pixel Record in the P-1 Stack makes accessing of that Pixel Record quick and efficient. With image information organized using the P-1 Stack in accordance with the present invention, it is possible to access a particular Image Intensity Data Array corresponding to a desired pixel location with an access time on the order of milliseconds.

Once the Pixel Record for is retrieved, since the structure of an Image Intensity Data Array for a pixel inherently defines the spectrum of that pixel, the presentation of that spectrum is simplified.

THRESHOLD ("P-2") PIXEL STACK The second data organization in accordance with a second embodiment of the present invention is the Thresholded Pixel Stack, also termed a "P-2 Stack".

The inclusive pixel stack is, as discussed, a data record that includes image intensity information from every pixel in the visual and corresponding electronic image, regardless of whether that intensity information is derived from light scattered from a portion of a microparticle corresponding to the particular pixel or from another feature or background. However, as may be appreciated by examination of FIG. 2, only a relatively small fraction of the pixels in an image correspond to locations on a microparticle. It is thus apparent that significant compression of image data may be achieved by not storing intensity information derived from pixels other than those pixels corresponding to a portion of a microparticle. This deletion is accomplished in the Thresholded Pixel Stack using a thresholding technique to be described.

Figure 12:
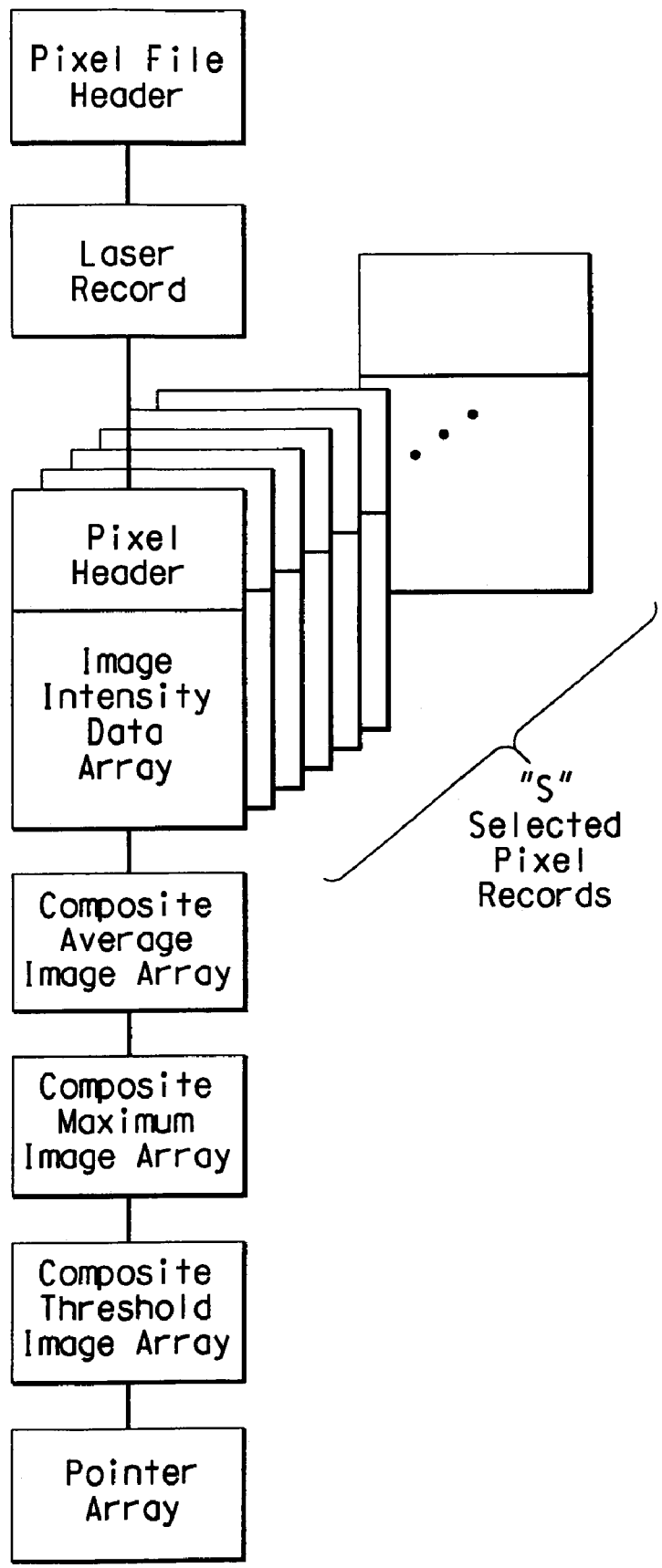
FIG. 12 is a diagrammatic representation, similar to FIG. 5, showing of the organization of the data structure formed in the implementation of a Threshold ("P-2") pixel stack in accordance with the present invention.
Figure 13:
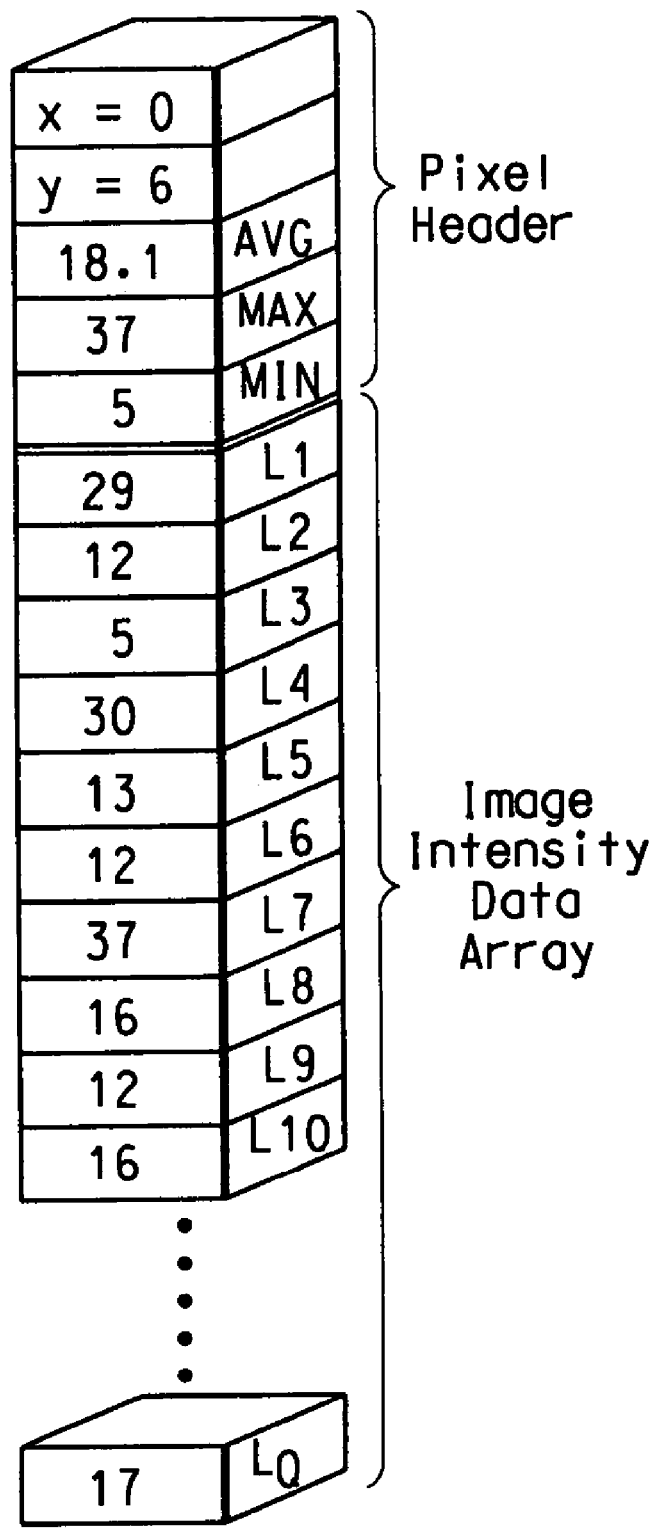
FIG. 13 is a diagrammatic representation of a Pixel Record in a Threshold ("P-2") pixel stack.

FIG. 12 is a diagrammatic representation, similar to FIG. 5, showing of the organization of the data structure of a Thresholded ("P-2") Pixel Stack formed in accordance with the present invention. FIG. 13 is a diagrammatic representation of an individual Pixel Record in a Thresholded Pixel Stack.

As with the inclusive P-1 stack, the Thresholded Pixel Stack includes a Pixel File Header file, files relating to the illuminating laser, a collection of pixel records, a Composite Average Image Array and a Composite Maximum Image Array.

The Thresholded Pixel Stack also includes two additional composite arrays, the Composite Thresholded Image Array (discussed in connection with FIG. 16) and a Pointer Array (discussed in connection with FIG. 17). Both of these arrays are multi-dimensional arrays that mirror the matrix (or whatever shaped) layout of the pixels in the image plane.

The data structure of the Pixel Record included within the Thresholded Pixel Stack is substantially similar to that the structure of a Pixel Record included in a P-1 Stack. As seen from a comparison of FIGS. 6A and 13, the Pixel Header in a Pixel Record of the Thresholded Pixel Stack differs in that it also includes information regarding the average image intensity of the pixel.

The collection of Pixel Records in the Thresholded Pixel Stack is significantly different from the counterpart structure in the inclusive P-1 Stack in that the P-2 Stack does not include all Pixel Records in the image. The Thresholded Pixel Stack includes only a select set of S number of Pixel Records (where S is less than N). Only Pixel Records whose Image Intensity Data Array includes at least one intensity value that is in excess of a predetermined analog threshold value are selected for inclusion in the collection of Pixel Records in a Thresholded Pixel Stack. If an Image Intensity Data Array does not contain a single value above the threshold, that array is not included in the Thresholded Pixel Stack.

A tabulated form of a select set of S number of Pixel Records in a Thresholded Pixel Stack selected in the manner to be described is given in FIG. 14. The row denoted "Order of Selection" records the order in which a Pixel Record is taken into the select set.

Figure 15:
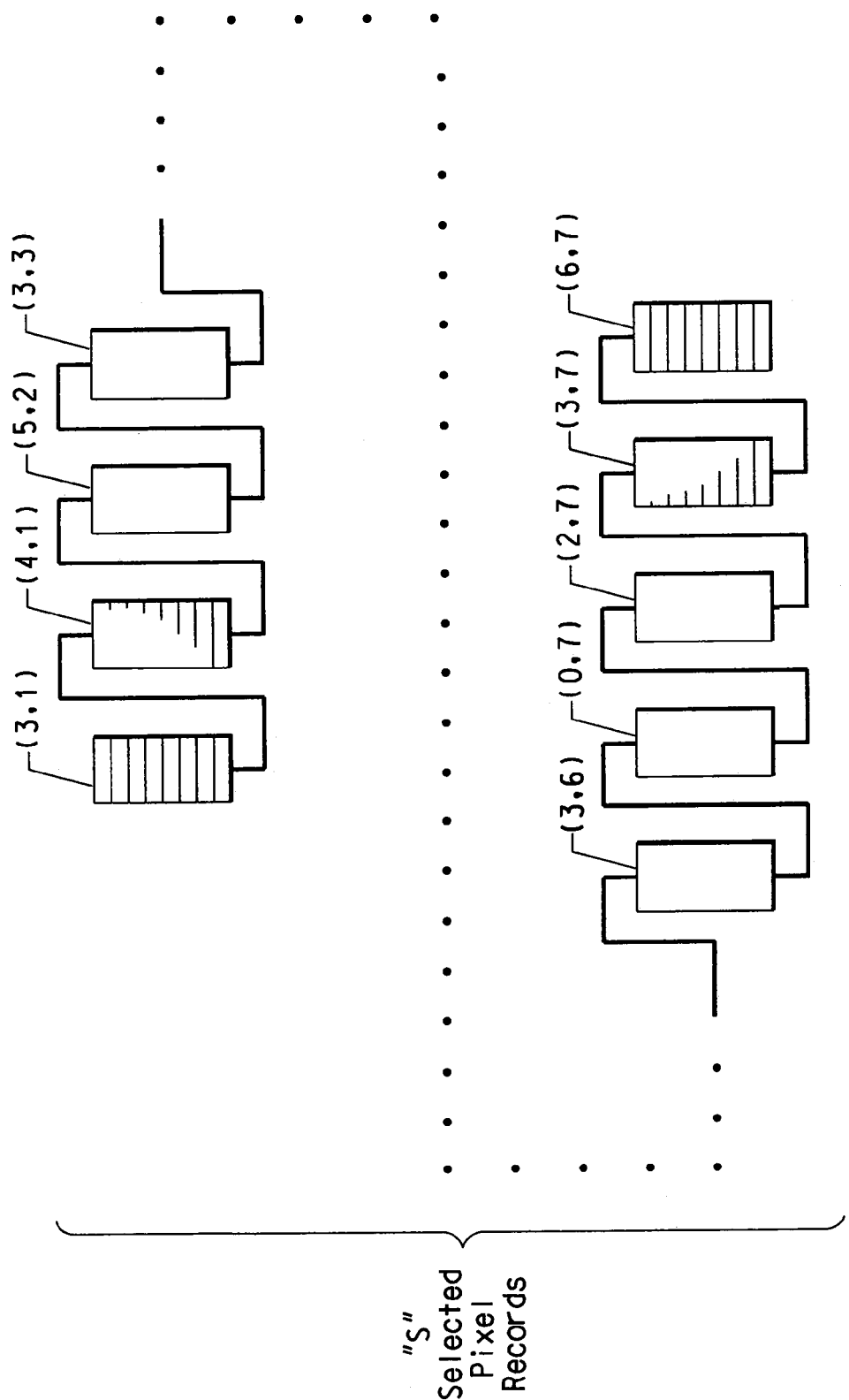
FIG. 15 is a graphical representation of a data structure comprising the collection of Pixel Records for an inclusive ("P-1") pixel stack as tabulated in FIG. 14.

FIG. 15 illustrates that the data structure of the collection of Pixel Records in a Thresholded Pixel Stack has the form of a linear array of linear arrays of data, similar to the form of the Pixel Record collection in an inclusive stack.

The initial operation in the creation of a Analog Threshold based upon the highest and lowest pixel values in the Q images. These values are identified in a manner generally similar to that discussed in connection with the creation of the P-1 stack. For each of the Q images in the scan all pixel locations are interrogated, raster fashion, and various Composite Image Arrays, such as a Composite Average Image Array, a Composite Maximum Image Array and a Composite Minimum Image Array are created. The highest and lowest intensity values are identified. It should be understood that although the following description focuses on the use of the Composite Maximum Image Array, any of the Composite Image Arrays described for the P-1 Stack may be used in an analogous manner, thus the use of any of these Composite Image Arrays is within the scope of the invention.

The Analog Threshold is calculated using the highest and lowest intensity values. The Analog Threshold value may be any appropriate functional relationship of the Highest Pixel Value and the Lowest Pixel Value. A convenient method to define the threshold is to add an offset to the lowest intensity value. A convenient offset to utilize is the Highest Pixel Value scaled by an appropriate scale factor. The scale factor may be predetermined from experience, or may be selected by interaction with a user.

Such a functional relationship involving the Highest Pixel Value, the Lowest Pixel Value and a Scale Factor could take the form:

Analog Threshold=Lowest Pixel Value+(Highest Pixel Value·Scale Factor)

Other relationships to define the Analog Threshold could be used.

The Pixel Records are selected for inclusion in the Thresholded Pixel Stack on the basis of a pixel-by-pixel comparison of the values in the Composite Maximum Image Array and the Analog Threshold.

These operations will become clearer with reference to FIGS. 14 through 17. It is assumed for this discussion that the Composite Maximum Image Array of FIG. 9 has been created and that the Analog Threshold value has been calculated as a value twenty (20) (an arbitrary value chosen for illustrative purposes).

Scanning through the Composite Maximum Image Array in raster order (using increasing X values at each value of Y value) the first pixel encountered whose maximum intensity value exceeds the Analog Threshold is the pixel (3,1). The Pixel Record corresponding to this pixel becomes the first Pixel Record selected for inclusion within the select set of Pixel Records contained in the Thresholded Pixel Stack (FIGS. 14, 15).

Since Pixel Records are selected for inclusion in a non-consecutive fashion some indication that correlates the raster order position of a selected Pixel Record with its position in the collection of pixel records must be provided. This function is served by the Pointer Array.

Upon the selection of a given Pixel Record the location in the Pointer Array corresponding to that pixel is updated with a sequential ordinal indicator denoting the order of selection of the Pixel Record from that pixel into the collection of pixel records. In the example being developed the ordinal "1" is loaded into the location in the Pointer Array corresponding to the pixel (3,1) (FIG. 17).

The value of the Composite Maximum Image Array in the location under test ("25") is loaded into the corresponding location in the Composite Thresholded Image Array (FIG. 16).

Continuing raster-wise to test the values in the Composite Maximum Image Array, the next pixel location whose maximum value exceeds the Analog Threshold is the pixel (4,1). Accordingly, the Pixel Record corresponding to this pixel (4,1) becomes the second entrant selected for inclusion into the collection of Pixel Records for the P-2 stack under construction (FIGS. 14, 15). The ordinal "2" is loaded into the location in the Pointer Array corresponding to the pixel (4,1) (FIG. 17). The maximum intensity value of this pixel (4,1) (i.e., "28") is loaded into the corresponding location in the Composite Thresholded Image Array (FIG. 15).

This examination continues in sequence until the full raster is completed and all qualifying Pixel Records have been identified and included into the collection.

It should be noted that even though the maximum values of pixels (3,2), (6,3), (6,4) and (6,6) contain image intensity values that are above background intensities, these Pixel Records are not selected for inclusion in the collection because the maximum intensity is less than the Analog Threshold.

Program Listing A pseudocode listing of a program for the creation of a P-2 stack is created is set forth on pages A-2 and A-3 of the Appendix. References in the following discussion are again keyed to the corresponding line numbers in the pseudocode listing. The variables "Q", "W" and "H" again respectively refers to the number of images, the number of pixels in the Width of each image, and the number of pixels in the Height of each image.

In order to compute the Analog Threshold the Lowest Pixel Value and Highest Pixel Value in the Q images must be identified. This task is accomplished in Lines 37 to 63.

The array "Image Intensity Data Array" is dimensioned as a (Q×1) array [i.e., from subscripts "0" to "(Q−1)"] in Line 37.

The "Composite Maximum Image Array" and "Composite Average Image Array" are each dimensioned as a (W×H) array [i.e., in the Width dimension from subscripts "0" to "(W−1)" and in the Height dimension from subscripts "0" to "(H−1)"] in Lines 38 and 39. Three additional (W×H) arrays, viz., the "Composite Minimum Image Array", the "Composite Threshold Image Array" and the "Pointer Array" are dimensioned in Lines 40, 41 and 42, respectively.

Initial Values in the buffers "LowestPixelValue" and "HighestPixelValue" are set to the same values as in the case of the P-1 Stack in Lines 43 and 44.

The Q images are interrogated to identify the highest and lowest intensity values in all Q images.

The Y values of all pixel locations are looped in an outer loop extending from Lines 45 to 63. For each Y value, the X values of the pixel locations are incremented in a first nested inner loop from Lines 46 to 62.

The utility "GetPixel" is called in Line 47. The pixel intensity values from the store of digital image representations ("MyImages") are retrieved and placed into the array "Image Intensity Data Array" in the same manner as discussed in connection with the P-1 Stack (Line 13).

The buffers "Sum" and "Max" and "Min" are initialized to zero (Lines 48 and 49). The buffers "Min" is initialized to a value higher than any expected intensity (Line 50).

For each X value within the "X" loop, a nested loop (Lines 51 to 58) sequentially reads the array "Image Intensity Data Array" through all of Q values [0 to (Q−1)].

On each iteration through the Q values several things occur, viz.:

- the buffer "Sum" is increased by the then-current Pixel Value (Line 53);
- the then-current Pixel Value is compared to the current value in the Max buffer. If the comparison is "True" the value in the Max buffer is changed to the current value (Line 54);
- the then-current Pixel Value is compared to the current value in the Min buffer. If the comparison is "True" the value in the Min buffer is changed to the current value (Line 55);
- the then-current Pixel value is also compared to the current LowestPixelValue and HighestPixelValue in these buffers (Lines 56 and 57). If either comparison is "True" the value in the appropriate buffer is changed.

The average pixel value (equal to "Sum" divided by the number of images Q) is loaded into the then-current (X, Y) pixel location in the "Composite Average Image Array" (Line 59). The then-current (X, Y) pixel location in both the "Composite Maximum Image Array" and the "Composite Minimum Image Array" are loaded with the values in the Max and Min buffers, respectively (Lines 60, 61).

The X value is then incremented (Line 62) and the "X" loop (Lines 46 to 62) iteratively repeated for each updated then-current (X,Y).

After all X looping is complete, the Y value is incremented (Line 63) and the full "Y" loop (Lines 45 to 63) iteratively repeated for all values of Y.

At the completion of the Y loop:

- the "Composite Average Image Array", the "Composite Maximum Image Array", the "Composite Minimum Image Array", each derived from all of the Q images, have been created (each iteration of Lines 59, 60 and 61, respectively); and
- the highest and lowest intensity values in all the images have been identified and stored in the buffers HighestPixelValue and LowestPixelValue (Lines 56, 57, respectively).

The value of the Analog Threshold is computed in Line 64. The Analog Threshold is shown using functional notation, indicating that the Analog Threshold is a function of the HighestPixelValue, LowestPixelValue and an appropriate Scale Factor. The Scale Factor may be interactively determined by a user, if desired.

The binary "P-2 Stack" file is then opened on disk (or other medium) in Line 65.

The files "PixelFileHeader" and "LaserRecord" are created on the disk in Lines 66 and 67.

Those pixel Records qualifying for inclusion in the set of Selected Pixel Records are chosen in Lines 68 to 85.

A Selected Pixel Record Number counter is initialized to zero in Line 68.

The Y values of the pixel locations are looped in an outer loop from Lines 69 to 85. For each Y value, the X values of the pixel locations are incremented in a first nested inner loop from Lines 70 to 84.

The Composite Maximum Image Array is then interrogated in raster fashion. For each "X" value within the "X" loop the value in the Composite Maximum Image Array stored at the then-current X and Y values is tested against the Analog Threshold using an "If" statement (Lines 71 to 83).

If the comparison is "True", that is, if the stored maximum value exceeds the Analog Threshold, then:

the then-current X and Y values of the pixel are loaded into the Selected Pixel Header (Lines 72 and 73);

the Selected Pixel Record Number counter is incremented (Line 74);

the updated value in the Selected Pixel Record Number counter is loaded into the then-current pixel location in the Pointer Array (Line 75);

the value of the Composite Maximum Image Array under test is loaded into the corresponding pixel location in the Composite Thresholded Image Array (Line 76);

the utility "GetPixel" is again invoked in Line 77 to retrieve the all Q intensity values from the selected pixel and to populate the Image Intensity Data Array for the selected pixel;

the values at the then-current pixel in the Composite Average Image Array, the Composite Maximum Image Array and the Composite Minimum Image Array are loaded into Pixel Header for this Selected Pixel Record (Lines 78 to 80); and the Selected Pixel Record Header and the Image Intensity Data Array are then saved to disk (Lines 81, 82).

The X value is then incremented (Line 84) and the "X" loop (Lines 70 to 84) iteratively repeated for each updated then-current (X,Y).

After all X looping is complete, the Y value is incremented (Line 32) and the full "Y" loop (Lines 69 to 85) iteratively repeated for all values of Y.

At the completion of the Y loop the "Pixel Header" and the "Image Intensity Data Array" for each Selected Pixel Record has been created and stored to disk (each iteration of Lines 81 and 82); and the "Composite Thresholded Image Array" has been created (each iteration of Line 76).

The earlier created "Composite Average Image Array" (Line 59), "Composite Maximum Image Array" (Line 60), and "Composite Minimum Image Array" (Line 61) are saved to disk in Lines 86, 87, 88, respectively.

The "Composite Threshold Image Array", is saved to disk in Line 89. The "Pointer Array", is saved to disk in Line 90.

The full, finished "Pixel File Header" (containing the number of Selected Pixel Records, the Lowest Pixel Value, the Highest Pixel Value and the Analog Threshold) is sent to disk for storage (Line 95).

The P-2 Stack closed (Line 96).

Advantages of the P-2 Stack Since the collection of Pixel Records in a P-2 stack includes only a selected set of S number of Pixel Records, the storage requirements for the overall P-2 stack is significantly reduced.

Using the Pointer Array, access and retrieval of individual Pixel Records is still efficiently accomplished. The ordinal value in the Pointer Array defines the Record Number ("R") used to calculate the Position of desired Pixel Record.

The inherency of spectral information within the structure of an Image Intensity Data Array is maintained.

The advantage of binary format is also kept.

-o-O-o-

Those skilled in the art having the benefit of the teachings of the present invention as hereinabove set forth may impart numerous modifications. Such modifications are to be construed as within the scope of the present invention, as defined by the appended claims.

---

PROGRAM APPENDIX

Creation of A P-1 Stack File
1 Open Binary File as #P-1 Stack
2 Put #P-1 Stack PixelFileHeader
3 Put #P-1 Stack LaserRecord
4 Dim Image Intensity Data Array [0 to (Q−1)]
5 Dim Composite Maximum Image Array [0 to (W−1), 0 to (H−1)]
6 Dim Composite Average Image Array [0 to (W−1), 0 to (H−1)]
7 LowestPixelValue = 3200
8 HighestPixelValue = 0
9 For Y = 0 to (H−1)
10   For X 0 to (W−1)
11     PixelHeader.X = X
12     PixelHeader.Y = Y
13     GetPixel MyImages(0), Q, bytes/pixel, W, X, Y, Image Intensity Data Array(0)
14     Sum = 0
15     Max = 0
16     For Pixel = [0 to (Q−1)]
17       PixelValue = Image Intensity Data Array(Pixel)
18       Sum = Sum + PixelValue
19       If PixelValue > Max Then Max = PixelValue
20       If PixelValue < LowestPixelvalue Then LowestPixelvalue = PixelValue
21       If PixelValue > HighestPixelValue Then HighestPixelValue = PixelValue
22     Next
23     PixelHeader.AvgPixel = Sum / Q
24     PixelHeader.MaxPixel = Max
25     Composite Average Image Array(X,Y) = Sum / Q
26     Composite Maximum Image Array(X,Y) = Max
27     Put #P-1 Stack PixelHeader
28     Put #P-1 Stack Image Intensity Data Array
29   Next X
30 Next Y
31 Put #P-1 Stack Compostite Average Image Array
32 Put #P-1 Stack Compostite Maximum Image Array
33 PixelFileHeader.LowestPixelValue = Lowest PixelValue
34 PixelFileHeader.HighestPixelValue = Highest PixelValue
35 Put PixelFileHeader into the "P-1 Stack" Binary File
36 Close the "P-1 Stack"Binary File
         Create P-2 Stack
37 Dim Image Intensity Data Array [0 to (Q−1)]
38 Dim Composite Maximum Image Array [0 to (W−1), 0 to (H−1)]
39 Dim Composite Minimum Image Array [0 to (W−1), 0 to (H−1)]
40 Dim Composite Average Image Array [0 to (W−1), 0 to (H−1)]
41 Dim Composite Threshold Image Array [0 to (W−1), 0 to (H−1)]
42 Dim Pointer Array [0 to (W−1), 0 to (H−1)]
43 LowestPixelValue = 3200
44 HighestPixelValue = 0
45   For Y = 0 to (H−1)
46     For X 0 to (W−1)
47       GetPixel MyImages(0), Q, bytes/pixel, W, X, Y, Image Intensity Data Array(0)
48       Sum = 0
49       Max = 0
50       Min = 3200

-continued

PROGRAM APPENDIX

```
51      For Pixel = [0 to (Q-1)]
52         PixelValue = Image Intensity Data
              Array(Pixel)
53         Sum = Sum + PixelValue
54         If PixelValue > Max Then Max = PixelValue
55         If PixelValue < Min Then Min = PixelValue
56         If PixelValue < LowestPixelvalue Then
              LowestPixelvalue = PixelValue
57         If PixelValue > HighestPixelvalue Then
              HighestPixelvalue = PixelValue
58      Next
59      Composite Average Image Array(X,Y) = Sum / Q
60      Composite Maximum Image Array(X,Y) = Max
61      Composite Mimimum Image Array(X,Y) = Min
62    Next X
63  Next Y
64  Analog Threshold = Function(LowestPixelValue, HighestPixelValue)
65  Open Binary File as P#-2 Stack
66  Put #P-2 Stack PixelFileHeader
67  Put #P-2 Stack LaserRecord
68  SelectedPixelRecordNumber = 0
69  For Y = 0 to (H-1)
70    For X = 0 to (W-1)
71      If Composite Maximum Image Array(X,Y) > Analog
            Threshold Then
72         SelectedPixelHeader.X = X
73         SelectedPixelHeader.Y = Y
74         SelectedPixelRecordNumber =
              SelectedPixelRecordNumber + 1
75         Pointer Array(X,Y) =
              SelectedPixelRecordNumber
76         Composite Threshold Image Array(X,Y) =
              Composite Maximum Image Array(X,Y)
77         GetPixel MyImages(0), Q, bytes/pixel, W, X,
              Y, Image Intensity Data Array(0)
78         SelectedPixelHeader.AvgPixel = Composite
              Average Image Array(X,Y)
79         SelectedPixelHeader.MaxPixel = Composite
              Maximum Image Array(X,Y)
80         SelectedPixelHeader.MinPixel = Composite
              Minimum Image Array(X,Y)
81         Put #P-2 Stack SelectedPixelHeader
82         Put #P-2 Stack Selected Image Intensity
              Data Array
83      End If
84    Next X
85  Next Y
86  Put #P-2 Stack Composite Average Image Array
87  Put #P-2 Stack Composite Maximum Image Array
88  Put #P-2 Stack Composite Mimimum Image Array
89  Put #P-2 Stack Composite Threshold Image Array
90  Put #P-2 Stack Pointer Array
91  PixelFileHeader.Pixels = SelectedPixelRecords
92  PixelFileHeader.LowestPixelValue = Lowest Pixel Value
93  PixelFileHeader.HighestPixelValue = Highest Pixel Value
94  PixelFileHeader.Threshold = Analog Threshold
95  Put #P-2 Stack PixelFileHeader
96  Close #P-2 Stack
```

What is claimed is:

1. A computer-implemented method for organizing image data representing light scattered from one or more substantially spherical microparticles, the method comprising the steps of:

(a) creating a digital representation of an image produced on an electronic image plane by light scattered from one or more substantially spherical microparticles at each of a predetermined number (Q) of illuminating wavelengths, a selected portion of each of the Q images corresponding to a region of interest on or adjacent to at least one microparticle, each selected portion of each image having a predetermined number (N) of pixels;

(b) for each of the N pixels in the selected portion of the image, creating an associated Image Intensity Data Array containing Q values, the Q values in at least some of the data arrays denoting the intensity of light at each of the Q wavelengths scattered from a location on a microparticle corresponding to the pixel associated with the data array;

(c) from the N Image Intensity Data Arrays, creating a select set of S number of Image Intensity Data Arrays, each Image Intensity Data Array in the select set having at least one intensity value that exceeds a predetermined analog threshold; and (d) creating a Pointer Array containing N values, the Pointer Array correlating the position on the electronic image plane of the pixel associated with each Image Intensity Data Array in the select set with the order of selection of that data array into the select set.

2. The method of claim 1 wherein the image on the electronic image plane is produced by light scattered by resonant Mie scattering.

3. The method of claim 1 further comprising the steps of:

(e) creating a Composite Image Array having N values, each value in the Composite Image Array being generated using a corresponding Image Intensity Data Array; and wherein the creation of the select set step (c) is performed by:

(f) scanning the Composite Image Array in a predetermined raster order and selecting an Image Intensity Data Array for inclusion in the select set on the basis of a comparison between the corresponding intensity value of the Composite Image Array and the predetermined analog threshold.

4. The method of claim 3 further comprising the step of:

(e) creating a Composite Thresholded Image Array containing N values, the Composite Thresholded Image Array being created by deleting from the Composite Image Array each value therein that is less than the predetermined analog threshold.

5. The method of claim 1 further comprising the step of:

(e) creating a Pixel File Header containing information regarding the value of the number "S" of Image Intensity Data Arrays in the select set and the value of the Analog Threshold.

6. A computer-implemented method for organizing image data representing light scattered from one or more substantially spherical microparticles, the method comprising the steps of:

(a) creating a digital representation of an image produced on an electronic image plane by light scattered from one or more substantially spherical microparticles at each of a predetermined number (Q) of illuminating wavelengths, each of the Q images having a predetermined number (N) of pixels;

(b) for each of the N pixels, creating an associated Image Intensity Data Array containing Q values, the Q values in at least some of the data arrays denoting the intensity of light at each of the Q wavelengths scattered from a location on a microparticle corresponding to the pixel associated with the data array;

(c) from the N Image Intensity Data Arrays, creating a select set of S number of Image Intensity Data Arrays, each Image Intensity Data Array in the select set having at least one intensity value that exceeds a predetermined analog threshold; and (d) creating a Pointer Array containing N values, the Pointer Array correlating the position on the electronic image plane of the pixel associated with each Image Intensity Data Array in the select set with the order of selection of that data array into the select set.

7. The method of claim 6 wherein the image on the electronic image plane is produced by light scattered by resonant Mie scattering.

8. The method of claim 6 further comprising the steps of:
(e) creating a Composite Image Array having N values, each value in the Composite Image Array being generated using a corresponding Image Intensity Data Array; and
wherein the creation of the select set step (c) is performed by:
(f) scanning the Composite Image Array in a predetermined raster order and selecting an Image Intensity Data Array for inclusion in the select set on the basis of a comparison between the corresponding intensity value of the Composite Image Array and the predetermined analog threshold.

9. The method of claim 8 further comprising the step of:
(e) creating a Composite Thresholded Image Array containing N values, the Composite Thresholded Image Array being created by deleting from the Composite Image Array each value therein that is less than the predetermined analog threshold.

10. The method of claim 6 further comprising the step of:
(e) creating a Pixel File Header containing information regarding the value of the number "S" of Image Intensity Data Arrays in the select set and the value of the analog threshold.

11. A computer-implemented method for organizing image data representing light scattered from one or more substantially spherical microparticles, the method comprising the steps of:
(a) creating a digital representation of an image produced on an electronic image plane by light scattered from one or more substantially spherical microparticles at each of a predetermined number (Q) of illuminating wavelengths, a selected portion of each of the Q images corresponding to a region of interest on or adjacent to at least one microparticle, each selected portion of each image having a predetermined number (N) of pixels;
(b) for each of the N pixels in the selected portion of the image, creating an associated Image Intensity Data Array containing Q values, the Q values in at least some of the data arrays denoting the intensity of light at each of the Q wavelengths scattered from a location on a microparticle corresponding to the pixel associated with the data array; and
(c) creating a Composite Image Array having N values, each value in the Composite Image Array being generated using a corresponding Image Intensity Data Array.

12. The method of claim 11 wherein the image on the electronic image plane is produced by light scattered by resonant Mie scattering.

13. A computer-implemented method for organizing image data representing light scattered from one or more substantially spherical microparticles, the method comprising the steps of:
(a) creating a digital representation of an image produced on an electronic image plane by light scattered from one or more substantially spherical microparticles at each of a predetermined number (Q) of illuminating wavelengths, each of the Q images having a predetermined number (N) of pixels;
(b) for each of the N pixels, creating an associated Image Intensity Data Array containing Q values, the Q values in at least some of the data arrays denoting the intensity of light at each of the Q wavelengths scattered from a location on a microparticle corresponding to the pixel associated with the data array; and
(c) creating a Composite Image Array having N values, each value in the Composite Image Array being generated using a corresponding Image Intensity Data Array.

14. The method of claim 13 wherein the image on the electronic image plane is produced by light scattered by resonant Mie scattering.

* * * * *

UNITED STATES PATENT AND TRADEMARK OFFICE
CERTIFICATE OF CORRECTION

| | | |
|---|---|---|
| PATENT NO. | : 7,612,769 B2 | Page 1 of 1 |
| APPLICATION NO. | : 11/224600 | |
| DATED | : November 3, 2009 | |
| INVENTOR(S) | : Lee J Heineman | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1087 days.

Signed and Sealed this

Nineteenth Day of October, 2010

David J. Kappos
*Director of the United States Patent and Trademark Office*